US010774036B2

(12) United States Patent
Kleinbeck-Riniker et al.

(10) Patent No.: US 10,774,036 B2
(45) Date of Patent: Sep. 15, 2020

(54) PROCESS FOR EARLY SACUBITRIL INTERMEDIATES

(71) Applicant: Novartis AG, Basel (CH)

(72) Inventors: Florian Karl Kleinbeck-Riniker, Zurich (CH); Tobias Kapferer, Basel (CH); Hongyong Kim, Changsu (CN); Jie Ku, Changsu (CN); Kurt Laumen, March (DE); Yunzhong Li, Suzhou (CN); Wei Peng, Changsu (CN); Thomas Ruch, Freiburg (DE); Thierry Schlama, Buschwiller (FR); Yao Yang, Changsu (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/472,386

(22) PCT Filed: Dec. 20, 2017

(86) PCT No.: PCT/IB2017/058203
§ 371 (c)(1),
(2) Date: Jun. 21, 2019

(87) PCT Pub. No.: WO2018/116203
PCT Pub. Date: Jun. 28, 2018

(65) Prior Publication Data
US 2019/0359554 A1  Nov. 28, 2019

(30) Foreign Application Priority Data
Dec. 23, 2016  (WO) ................ PCT/CN2016/111674

(51) Int. Cl.
*C07C 227/06* (2006.01)
*C07C 229/36* (2006.01)
*C12P 41/00* (2006.01)

(52) U.S. Cl.
CPC .......... *C07C 227/06* (2013.01); *C07C 229/36* (2013.01); *C12P 41/006* (2013.01)

(58) Field of Classification Search
None
See application file for complete search history.

(56) References Cited

U.S. PATENT DOCUMENTS

| 9,624,163 B2 | 4/2017 | Zhu et al. | |
| 2016/0002688 A1* | 1/2016 | Quintanar-Audelo | ...................... C12N 9/1096 435/119 |
| 2018/0362439 A1* | 12/2018 | Chen | ...................... C07C 49/245 |

FOREIGN PATENT DOCUMENTS

| CN | 105026361 A | 11/2015 |
| CN | 105168205 A | 12/2015 |
| CN | 105884656 A | 8/2016 |
| WO | 14032627 A1 | 3/2014 |

OTHER PUBLICATIONS

Parmeggiani, F, et al., "Singly-Biocatalyst Synthesis of Enanttiopure D-Arylalanines Exploiting an Engineered D-Amino Acid Dehydrogenase", Advanced Synthesis & Catalysis, 358(20):3298-3306, 2016.
Ahmed, S. T., et al., "Chemoenzymatic Synthesis of Optically Pure L- and D-Biarylalanines through Biocatalytic Asymmetric Amination and Palladium-Catalyzed Arylation", ACS Catalysis, 5(9):5410-5413, 2015.
Park, E-S., and Shin, J-S., "Deracemization of Amino Acids by Coupling Transaminases of Opposite Stereoselectivity", Advanced Synthesis & Catalysis, 356(18):3505-3509, 2014.

* cited by examiner

Primary Examiner — Clinton A Brooks
Assistant Examiner — Jennifer C Sawyer
(74) Attorney, Agent, or Firm — Judith D. Kuntz

(57) ABSTRACT

The invention relates to a new enantioselective process for producing useful intermediates for the manufacture of NEP inhibitors or prodrugs thereof, in particular NEP inhibitors comprising a γ-amino-δ-biphenyl-α-methylalkanoic acid, or acid ester, backbone.

21 Claims, No Drawings

PROCESS FOR EARLY SACUBITRIL INTERMEDIATES

RELATED APPLICATIONS

This application is a national stage application, filed under 35 U.S.C. § 371, of International Application No. PCT/182017/058203, filed Dec. 20, 2017, which claims priority to and the benefit of, Chinese Patent Application No. PCT/CN2016/111674, filed Dec. 23, 2016, the entire contents of which are incorporated herein by reference in their entireties.

FIELD OF THE INVENTION

The present invention relates to a new chemical synthesis route for intermediates useful for the preparation of neprilysin (NEP) inhibitors and their prodrugs, in particular for the NEP inhibitor prodrug sacubitril.

BACKGROUND OF THE INVENTION

The NEP inhibitor prodrug sacubitril (N-(3-carboxyl-1-oxopropyl)-(4S)-(p-phenylphenylmethyl)-4-amino-(2R)-methyl butanoic acid ethyl ester; IUPAC name 4-{[(1S,3R)-1-([1,1'-biphenyl]-4-ylmethyl)-4-ethoxy-3-methyl-4-oxobutyl]amino}-4-oxobutanoic acid, also known as AHU377) is represented by the following formula (A)

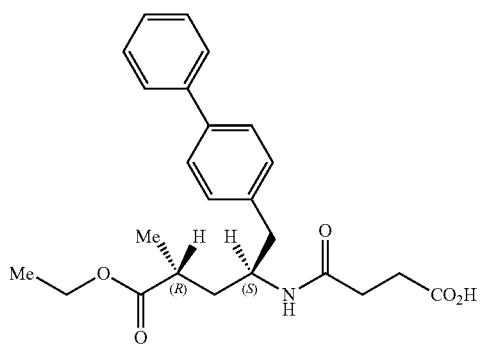

Sacubitril together with valsartan, a known angiotensin receptor blocker (ARB), forms a sodium salt hydrate complex, known as LCZ696, comprising the anionic forms of sacubitril and valsartan, sodium cations and water molecules in the molar ratio of 1:1:3:2.5, respectively (ratio of 6:6:18:15 in the asymmetric unit cell of the solid state crystal) (WO 2007/056546), and which is schematically present in formula (B).

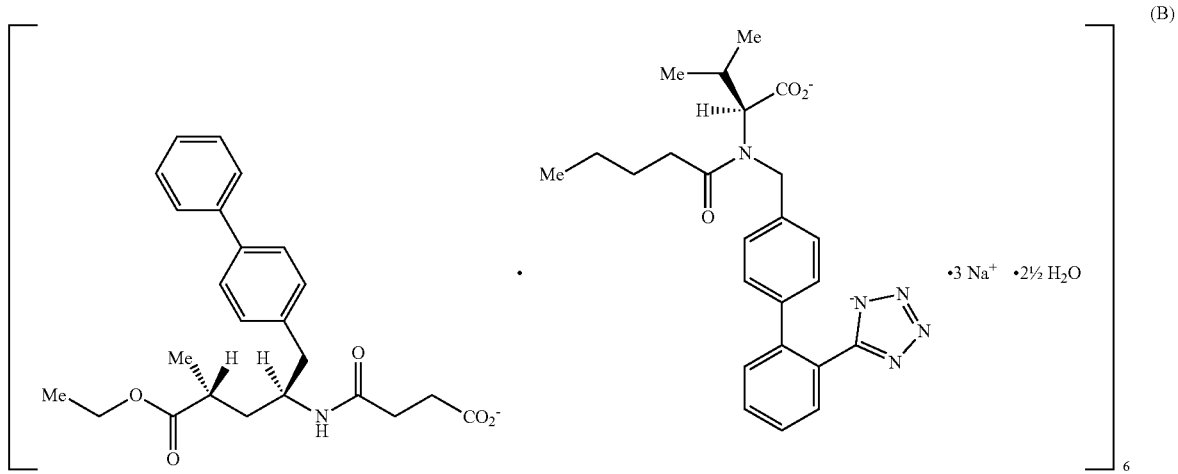

Said complex is also referred to by the following chemical names: trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate or octadecasodium hexakis(4-{[(1S,3R)-1-([1,1'-biphenyl]-4-ylmethyl)-4-ethoxy-3-methyl-4-oxobutyl]amino}-4-oxobutanoate) hexakis(N-pentanoyl-N-{[2'-(1H-tetrazol-1-id-5-yl)[1,1'-biphenyl]-4-yl]methyl}-L-valinate)-water (1/15) (IUPAC nomenclature).

LCZ696 acts as angiotensin receptor neprilysin inhibitor (ARNI) and is therefore useful particularly in the treatment of hypertension or chronic heart failure. Its utility has been confirmed by clinical trials, e.g. in the landmark PARADIGM-HF trial. Meanwhile, on Jul. 7, 2015, the FDA has approved LCZ696 for marketing.

Chemical synthesis routes to prepare NEP inhibitors and their prodrugs, in particular sacubitril, and its precursors have been described previously, e.g. in Ksander et al. J. Med. Chem. 1995, 38, 1689-1700; in U.S. Pat. No. 5,217,996 and in the international patent applications WO 2007/083774, WO 2007/083776, WO 2008/031567, WO 2008/083967, WO 2008/120567 WO 2009/090251, WO 2010/081410, WO 2011/035569, WO 2011/088797, WO 2012/025501, WO 2012/025502, WO 2013/026773, WO 2014/032627, WO 2015/024991, and WO 2015/037460 as well as in CN patent applications CN101362708, CN102260177, CN103483201, CN104557600, CN104725256, CN104725279, CN105017082, CN105061263, CN105085322, CN105152980, CN105168205, CN105198775, CN105237560, CN105330569, CN105481622, CN105566194, CN105601524 and CN105884656.

In particular CN101362708, WO 2013/026773, WO 2014/032627, WO 2015/024991 and CN105884656 deal with novel synthesis methods to provide the precursor compound

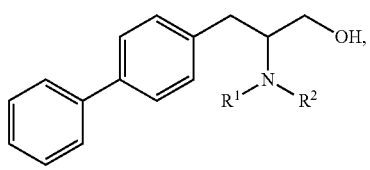
in particular
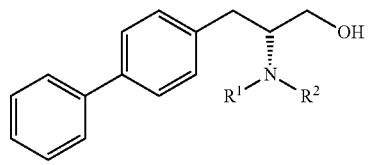
wherein R1 and R2 are independently of each other hydrogen or a nitrogen protecting group.
The process disclosed in WO 2013/026773 is depicted in the following scheme
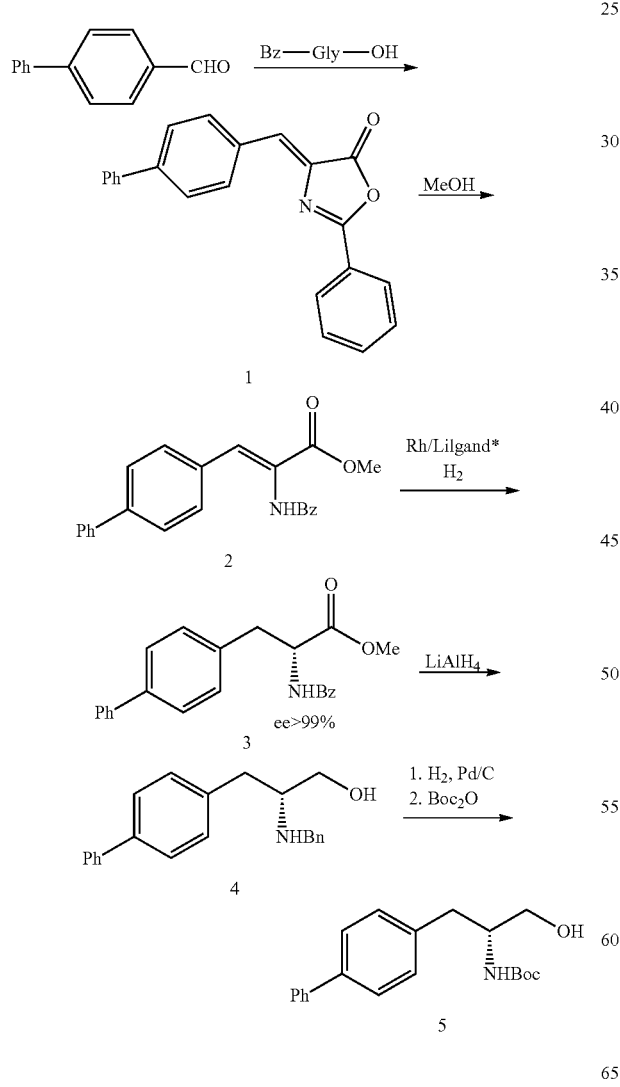
The process disclosed in CN101362708 is depicted in the following scheme
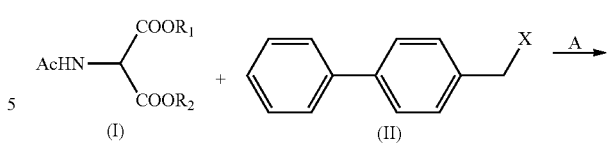
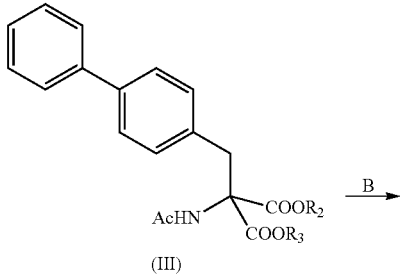
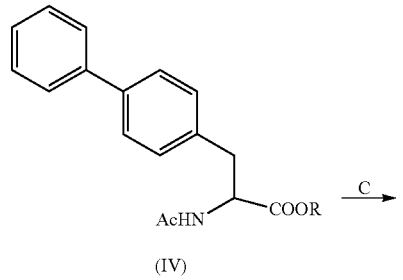
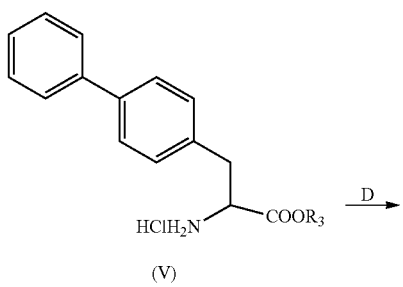
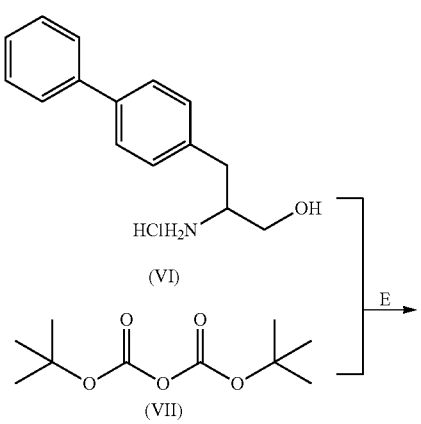

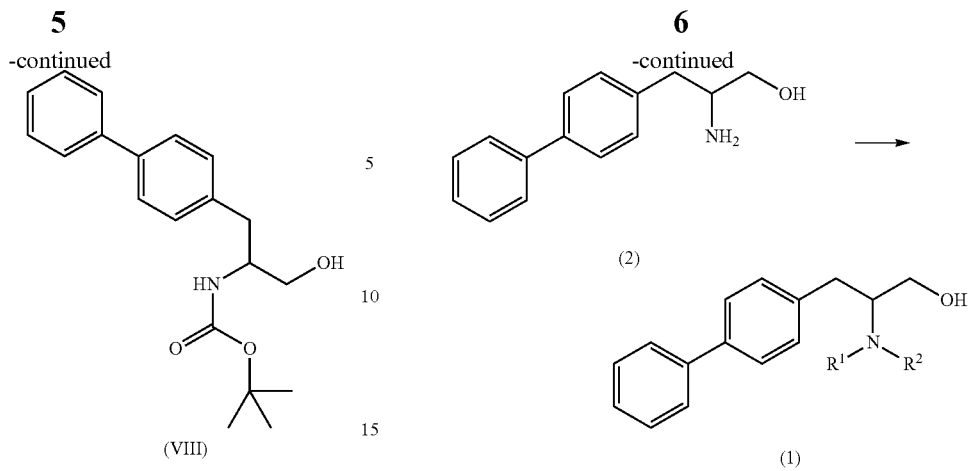
The process disclosed in WO 2014/032627 is depicted in the following scheme
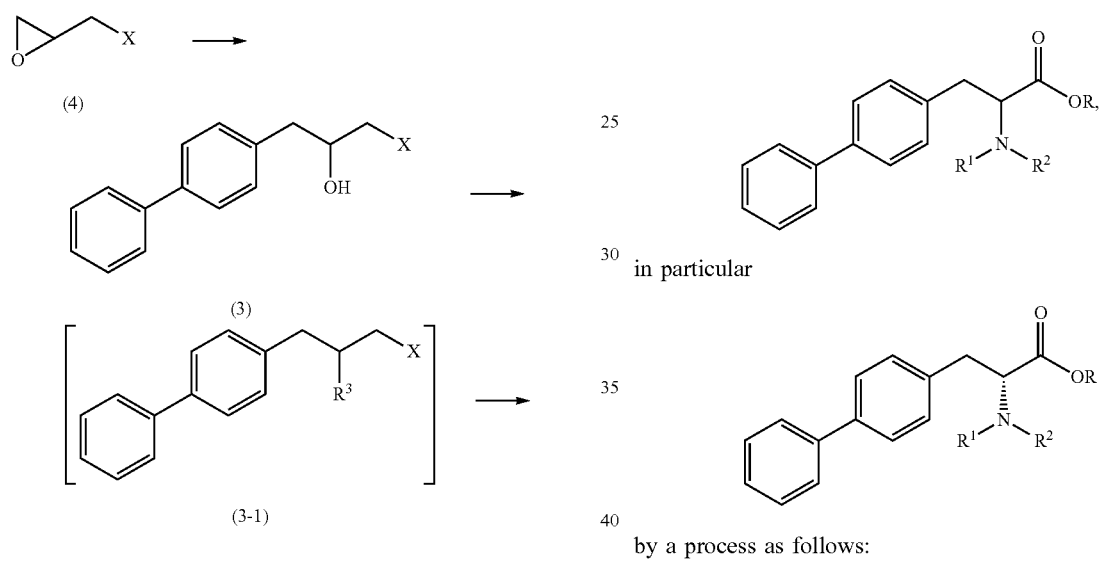
In addition, WO 2015/037460 discloses a process for obtaining an earlier intermediate, namely
in particular
by a process as follows:
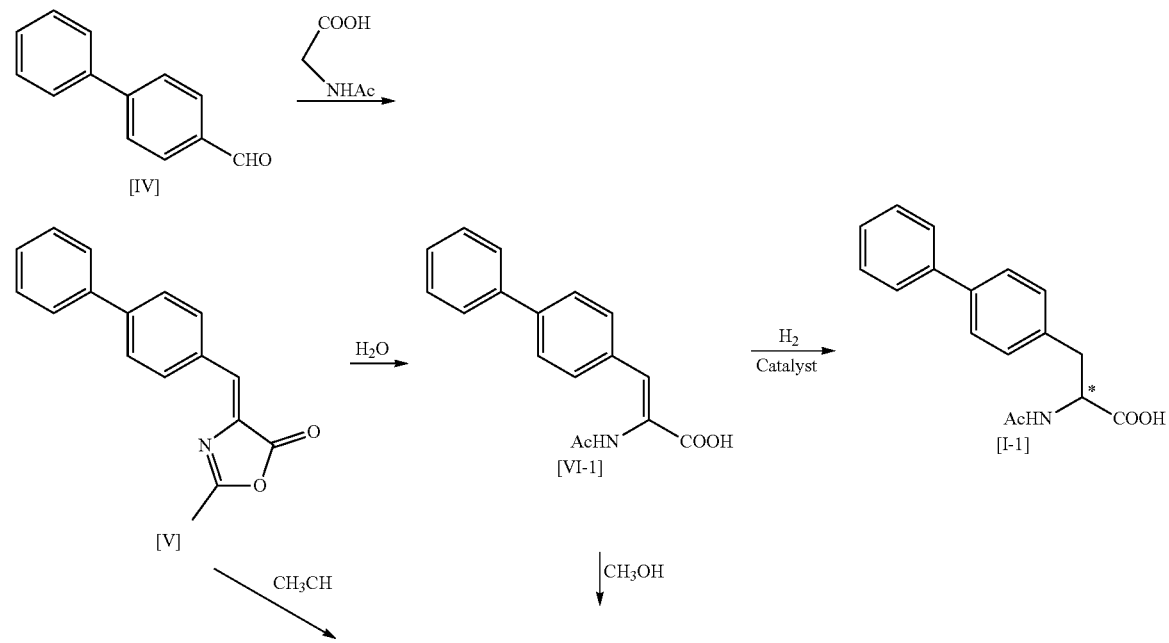

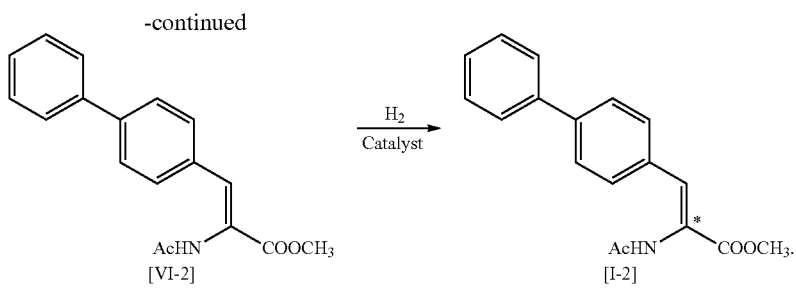

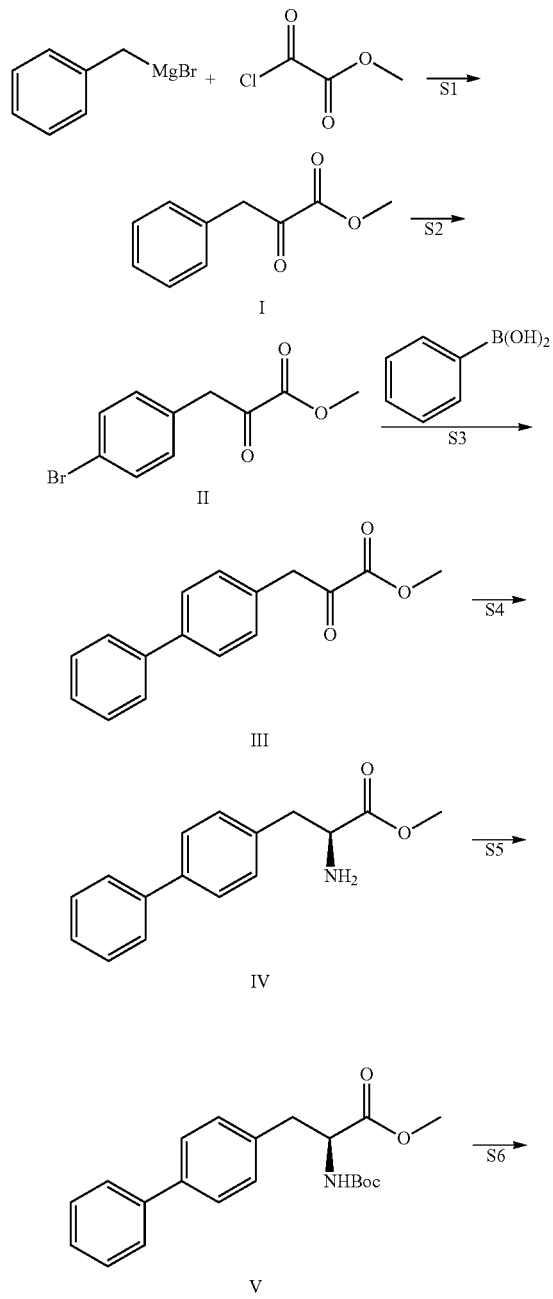

The process disclosed in CN105884656 is depicted in the following scheme

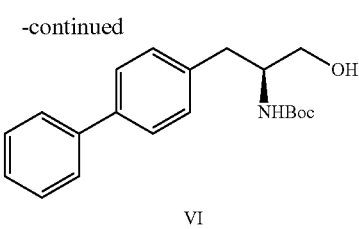

However, these processes still have disadvantages such as potentially dangerous reactants or use of expensive catalysts and/or limited stereo-selectivity. Therefore, there is still a need to design chemical processes to provide cheap ways to access said starting materials for the synthesis of sacubitril which are suitable for industrial scale production under economically and environmentally favorable conditions and provide such drug substance precursors in high chemical purity and with high stereo-chemical selectivity.

SUMMARY OF THE INVENTION

The invention relates to a novel process for the manufacture of a compound of formula (III), especially (III-a) represented below, including process steps for the manufacture of the educt as well as further process steps resulting in the manufacture of sacubitril.

Accordingly, in a first aspect, the present invention relates to a process for preparing a compound of formula (III), or a salt thereof

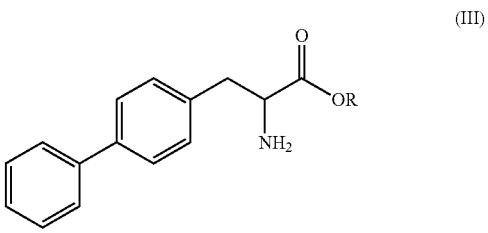

wherein R is hydrogen or a carboxyl protecting group, comprising converting a compound of formula (IV), or a salt thereof,

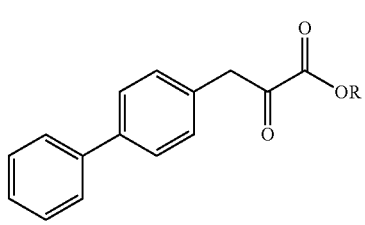

(IV)

wherein R is hydrogen or a carboxyl protecting group,
into the compound of formula (III) by bringing it in contact with an ω-transaminase in the presence of an achiral amine donor, wherein the conversion rate from the compound of formula (IV) to the compound of formula (III) is more than 50%.

In one embodiment thereof, the present invention relates to a process for preparing a compound of formula (III-a), or a salt thereof

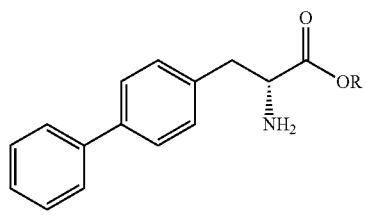

(III-a)

wherein R is hydrogen or a carboxyl protecting group,
comprising converting a compound of formula (IV), or a salt thereof,

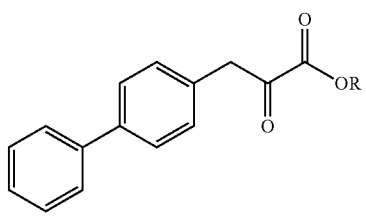

(IV)

wherein R is hydrogen or a carboxyl protecting group,
into the compound of formula (III-a) by bringing it in contact with an (R)-selective ω-transaminase in the presence of an amine donor of the general formula R'R"CH—NH$_2$, preferably an achiral amine donor, and a coenzyme, wherein the conversion rate from the compound of formula (IV) to the compound of formula (III-a) is more than 50%.

Further embodiments relate to particular reaction conditions of this reaction step as well as to associated process steps for producing the starting compound of formula (IV) and/or further reacting the obtained compound of formula (III) and (III-a), respectively, to finally obtain the NEP inhibitor compound sacubitril.

The reaction sequence including the key process step c involving the transaminase from a compound of formula (IV) to a compound of formula (III) and of formula (III-a), respectively, is depicted in the following SCHEME 1 and SCHEME 1-a, respectively:

SCHEME 1

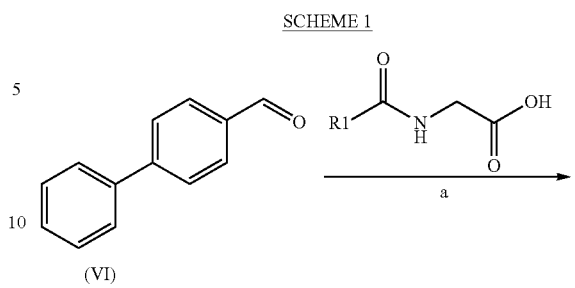

(VI)

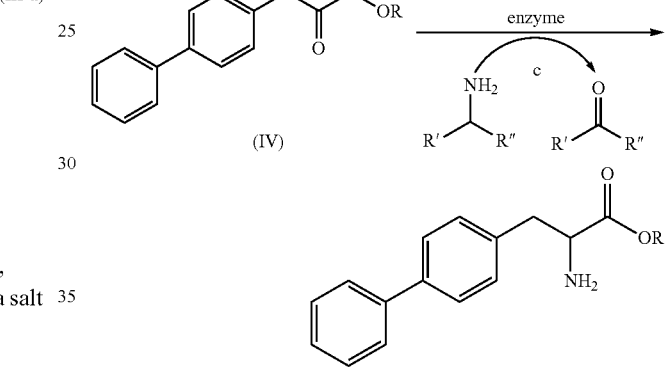

SCHEME 1-a

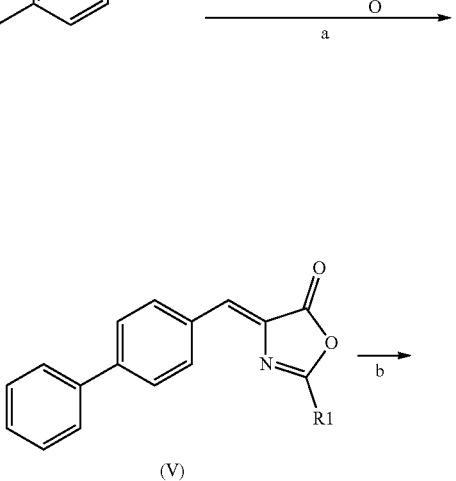

(VI)

(V)

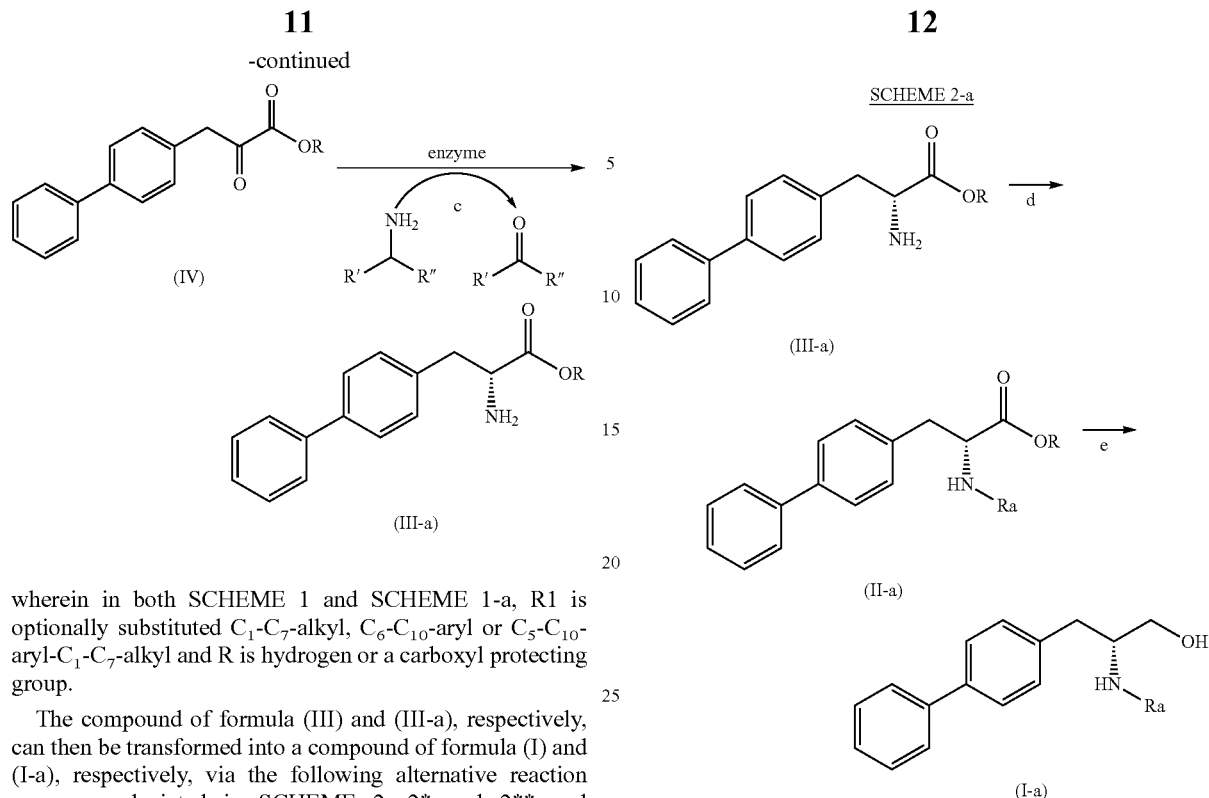

wherein in both SCHEME 1 and SCHEME 1-a, R1 is optionally substituted $C_1$-$C_7$-alkyl, $C_6$-$C_{10}$-aryl or $C_5$-$C_{10}$-aryl-$C_1$-$C_7$-alkyl and R is hydrogen or a carboxyl protecting group.

The compound of formula (III) and (III-a), respectively, can then be transformed into a compound of formula (I) and (I-a), respectively, via the following alternative reaction sequences depicted in SCHEME 2, 2* and 2** and SCHEME 2-a, 2*-a and 2**-a, respectively:

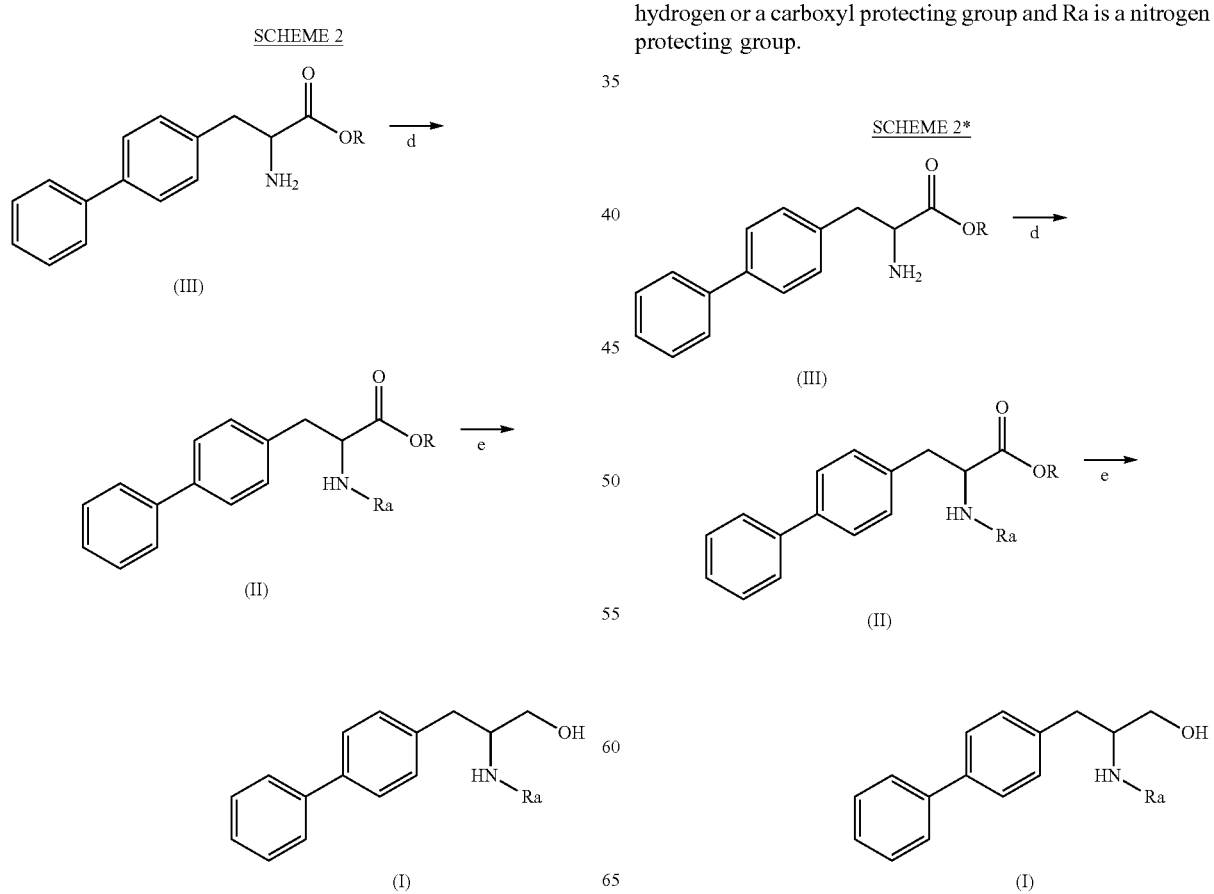

wherein in both SCHEME 2 and SCHEME 2-a, R is hydrogen or a carboxyl protecting group and Ra is a nitrogen protecting group.

SCHEME 2*-a

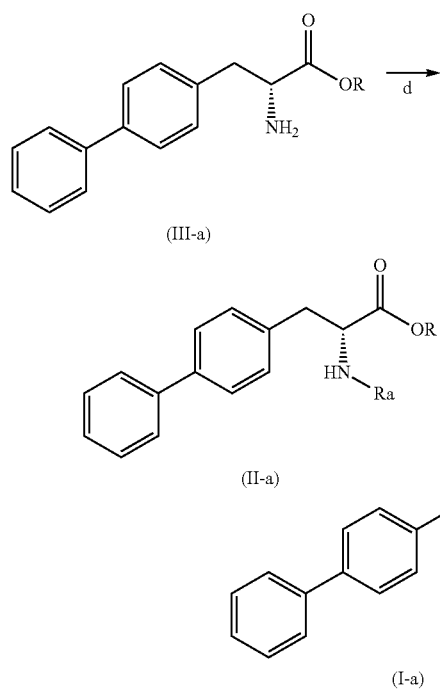

wherein in both SCHEME 2* and SCHEME 2*-a, R is optionally substituted $C_1$-$C_7$-alkyl, $C_6$-$C_{10}$-aryl or $C_6$-$C_{10}$-aryl-$C_1$-$C_7$-alkyl and Ra is a nitrogen protecting group.

SCHEME 2**

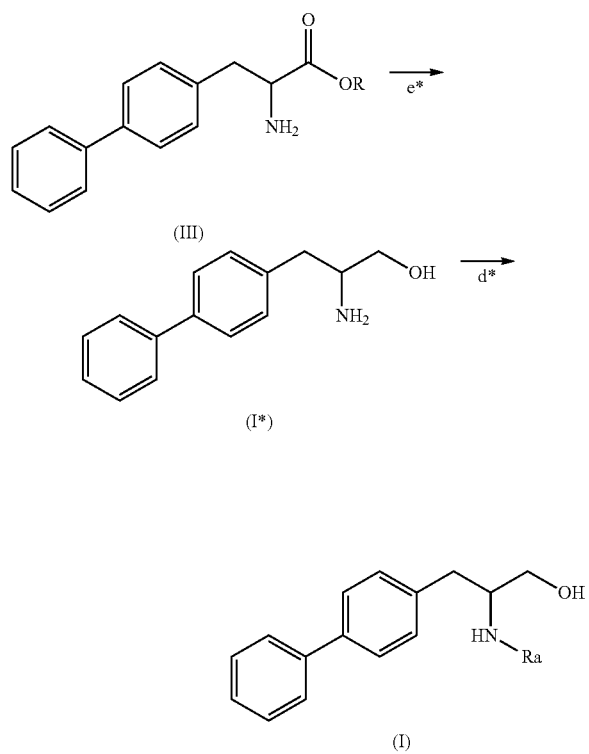

SCHEME 2**-a

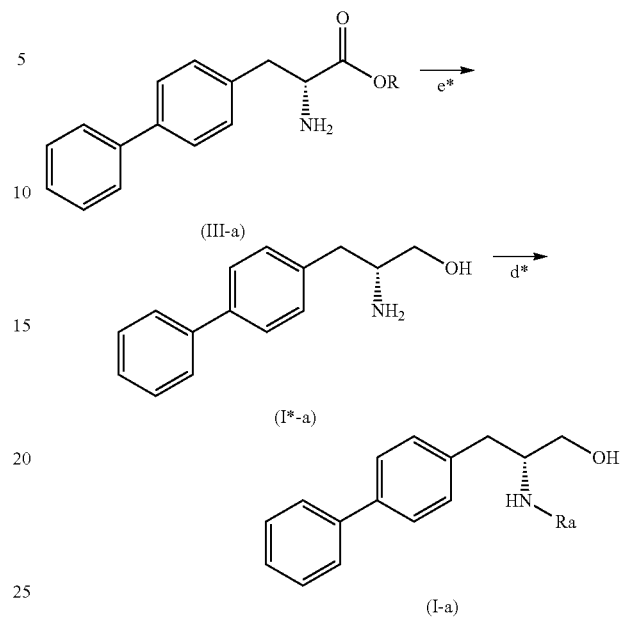

wherein in both SCHEME 2 and SCHEME 2-a, R is hydrogen or a carboxyl protecting group and Ra is a nitrogen protecting group.

The obtained compound of formula (I) and (I-a), respectively, can then be transformed into the NEP inhibitor compound sacubitril via known reaction steps as depicted in SCHEME 3 and SCHEME 3-a, respectively:

SCHEME 3

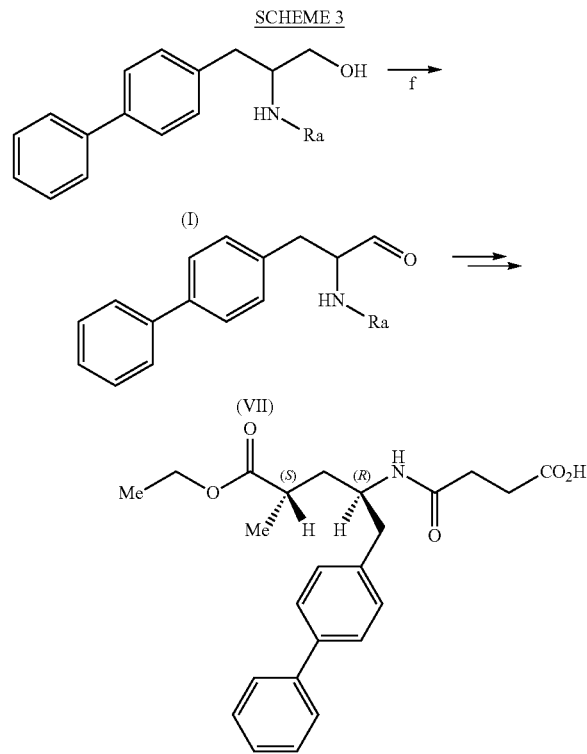

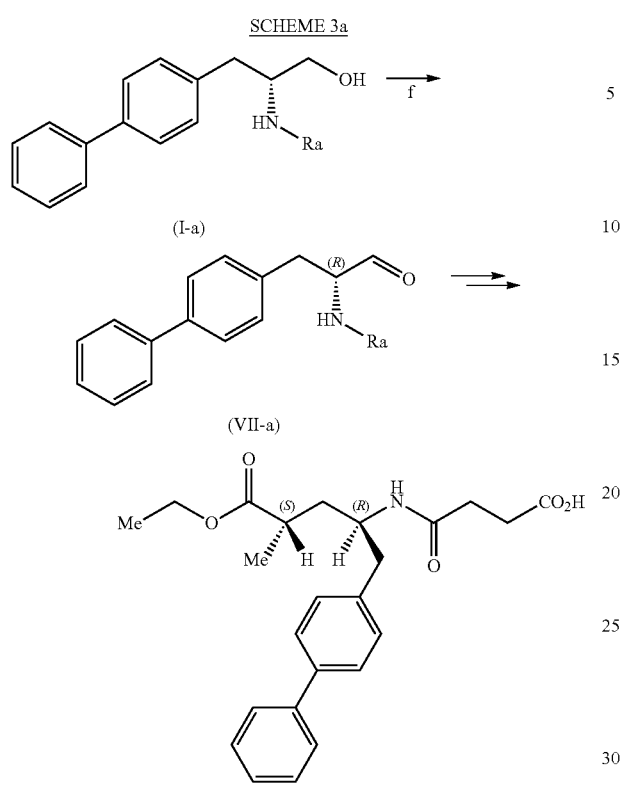
wherein in both SCHEME 3 and SCHEME 3-a, Ra is a nitrogen protecting group.
Furthermore, in a second aspect, the present invention relates to a process according to the following SCHEME 4 and SCHEME 4-a:

SCHEME 4-a

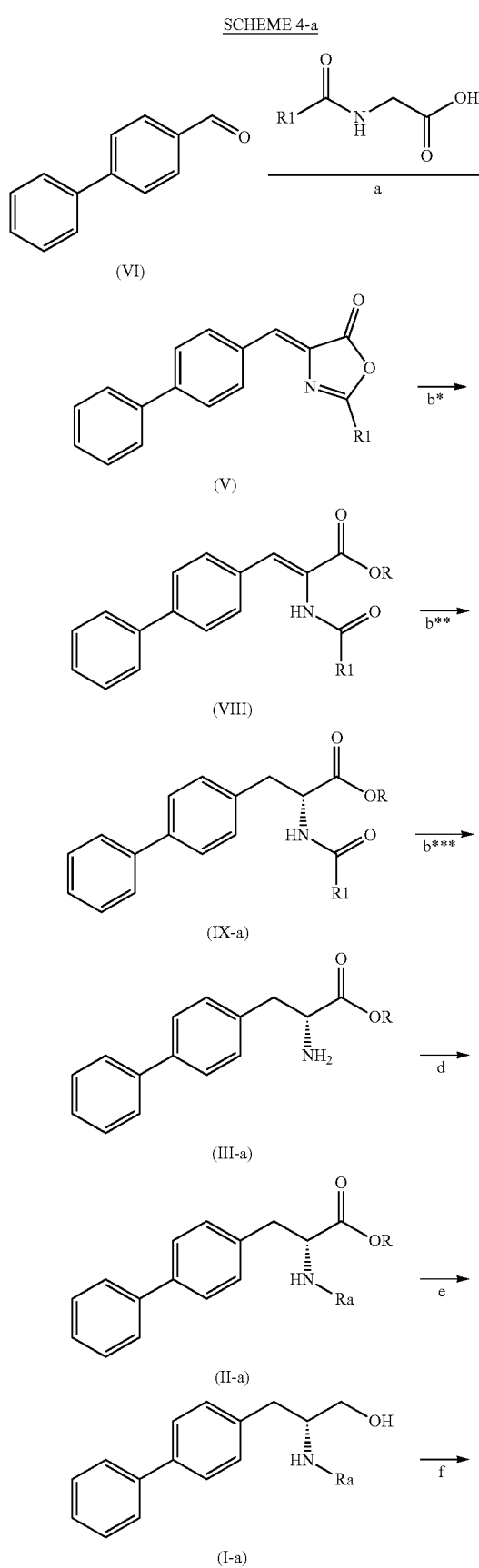

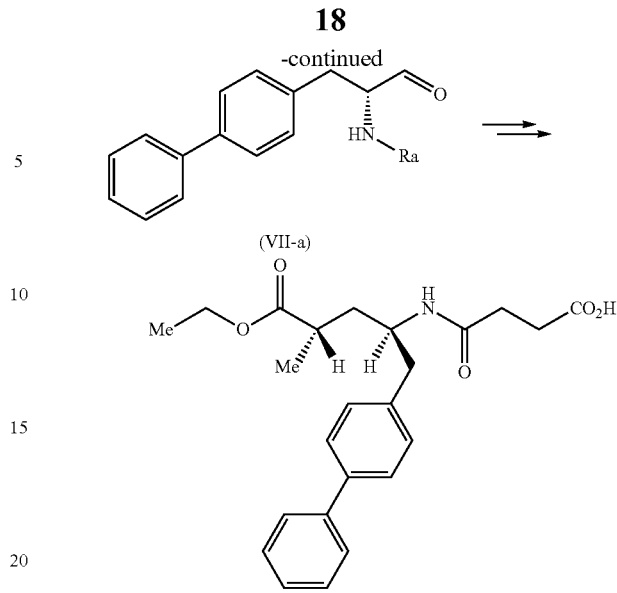

wherein in both schemes, the substituents have the following meanings: R is hydrogen or a carboxyl protecting group, R1 is optionally substituted $C_1$-$C_7$-alkyl, $C_6$-$C_{10}$-aryl or $C_6$-$C_{10}$-aryl-$C_1$-$C_7$-alkyl, and Ra is a nitrogen protecting group.

In its above mentioned aspects, which are also given in more detail below, the present invention provides the following advantages: The described novel synthesis routes are suitable for industrial scale processing, economically and environmentally favorable. The compounds of formula (III) which are intermediates desired for the synthesis of sacubitril can be produced with high yield and high stereoselectivity.

DETAILED DESCRIPTION OF THE INVENTION

General Terms

The general definitions used above and below, unless defined differently, have the following meanings, where replacement of one or more or all expressions or symbols by the more specific definitions can be made independently for each invention embodiment and lead to more preferred embodiments.

Where the plural form is used for compounds, starting materials, intermediates, salts, pharmaceutical preparations, diseases, disorders and the like, this intends to mean one (preferred) or more single compound(s), salt(s), pharmaceutical preparation(s), disease(s), disorder(s) or the like, where the singular or the indefinite article ("a", "an") is used, this does not intend to exclude the plural, but only preferably means "one".

Chiral Compounds

The term "chiral" refers to molecules which have the property of non-superimposability on their mirror image partner, while the term "achiral" refers to molecules which are superimposable on their mirror image partner.

In the formulae of the present application the term "〰〰〰" on a C-sp³ represents a covalent bond, wherein the stereochemistry of the bond is not defined. This means that the term "〰〰〰" on a C-sp³ comprises an (S) configuration as well as an (R) configuration of the respective chiral centre. Furthermore, mixtures, e.g. mixtures of enantiomers such as racemates, are also encompassed by the present invention. Especially preferred are single stereoisomers of the compounds of the formula (1) or (2), especially the specific ones of formula (1-a) and (1-b).

In the formulae of the present application the term "  " on a C-sp² represents a covalent bond, wherein the stereochemistry or the geometry of the bond is not defined. This means that the term "  " on a C-sp² comprises a (Z) configuration as well as a (E) configuration of the respective double bond. Furthermore, mixtures, e.g., mixtures of double bond isomers are also encompassed by the present invention.

In the formulae of the present application the term "  " on a C-sp³ indicates the absolute stereochemistry, either (R) or (S).

In the formulae of the present application the term "  " on a C-sp³ indicates the absolute stereochemistry, either (R) or (S).

In the formulae of the present application, the term " ---------- " indicates a C-sp²-C-sp³ bond or a C-sp²-C-sp² bond.

The compounds of the present invention can possess one or more asymmetric centers. The preferred absolute configurations are as indicated herein specifically. However, any possible pure enantiomer, pure diastereoisomer, or mixtures thereof, e.g., mixtures of enantiomers, such as racemates, are encompassed by the present invention.

Compounds with a stereogenic center but without indication of a specific configuration are considered mixtures of compounds with the respective configurations, e.g. R,R; R,S; S,R and SS, or pure enantiomers/diastereomers.

Stereoisomeric, especially enantiomeric, purity, is where mentioned referring to all diastereomers of the compound taken together (100%). It is determined by chiral chromatography (examples include HPLC, uPLC and GC) or NMR (with addition of chiral entities and or metals).

The term "substantially optically pure" compound, as defined herein, refers to a compound obtained by a process according to the invention wherein the compound has an optical purity of at least 70% (ee=enantiomeric excess), more preferably of at least 90% (ee) and most preferably at least 95% (ee) or more, such as 100% (ee).

Prodrugs

The term "pro-drug", as used herein, represents in particular compounds which are transformed in vivo to the parent compound, for example, by hydrolysis in blood, for example as described in T. Higuchi and V. Stella, "Pro-drugs as Novel Delivery Systems", volume 14 of the ACS Symposium Series; Edward B. Roche, editor, "Bioreversible Carriers in Drug Design", American Pharmaceutical Association and Pergamon Press, 1987; H Bundgaard, editor, "Design of Prodrugs", Elsevier, 1985; Judkins et al. *Synthetic Communications* 1996, 26, 4351-4367, and "The Organic Chemistry of Drug Design and Drug Action", second edition, R. B. Silverman (particularly chapter 8, pages 497-557), Elsevier Academic Press, 2004.

Pro-drugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Pro-drugs also include compounds convertible to the active drug by an oxidative or reductive reaction. As examples may be mentioned:
  Oxidative activation
    N- and O-dealkylation
    Oxidative deamination
    N-oxidation
    Epoxidation
  Reductive activation
    Azo reduction
    Sulfoxide reduction
    Disulfide reduction
    Bioreductive alkylation
    Nitro reduction
NEP Inhibitor The term "NEP inhibitor" describes a compound which inhibits the activity of the enzyme neutral endopeptidase (NEP, EC 3.4.24.11).

In the present invention the terms "NEP-inhibitor" or "NEP-inhibitor prodrug" relates to the substances as such or to salts thereof, preferably pharmaceutically acceptable salts thereof. Examples are sodium, potassium, magnesium, calcium or ammonium salts. Calcium salts are preferred.

The NEP inhibitor prodrug N-(3-carboxy-1-oxopropyl)-(4S)-p-phenylphenylmethyl)-4-amino-(2R)-methylbutanoic acid ethyl ester optionally may be further reacted to obtain the active NEP inhibitor N-(3-carboxy-1-oxopropyl)-(4S)-p-phenylphenylmethyl)-4-amino-(2R)-methylbutanoic acid, either in vitro or in vivo.

Transaminase

In the context of the present invention, a transaminase is a pyridoxal-phosphate-dependent enzyme catalysing the transfer of an amino group ($NH_2$) from a primary amine to a carbonyl group ($C=O$) of an acceptor molecule. Transaminases are classified in E.C. 2.6.1.X. In a particularly preferred embodiment of the present invention, the transaminase is an (R)- or (S)-selective transaminase, particularly is in a preferred embodiment an ω-transaminase, in particular an (R)-selective ω-transaminase.

In the context of the present invention an ω-transaminase is an enzyme preferably with the classification code E.C.2.6.1.18. These amino transaminases are characterised in that they mainly use amines as substrates. These enzymes are further characterised by exhibiting an equilibrium constant of ω-transaminase catalysed reactions which is greater than 1.

The present invention also understands under the term transaminase, in particular ω-transaminase, an extract of an organism, such as a microorganism or a cell, containing a transaminase, in particular an ω-transaminase, or a living or dead cell or microorganism itself comprising a transaminase, in particular an ω-transaminase. Such a microorganism or cell or extract or transaminase enzyme may be used in immobilised or non-immobilised form.

The transaminase, in particular the ω-transaminase, may also be a recombinantly produced naturally occurring (wild-type) or genetically modified transaminase, in particular an ω-transaminase, which is coded partially or completely by a nucleic acid sequence or a derivative thereof contained in one of the above-identified organisms or being equivalent thereto.

A recent overview of ω-transaminases which may be used and/or optimized to be used according to the present invention are described for instance in Koszelewski et al., *Trends in Biotechnology* 2010, 28, 324-332, and Malik et al., *Appl. Microbiol. Biotechnol.* 2012, 94, 1163-1171. Such transaminases can be obtained e.g. from microorganisms like *Chromobacterium violaceum, Vibrio fluvialis, Alcaligenes denitrificans, Klebsiella pneumoniae, Bacillus thuringiensis* and others.

In one embodiment, the ω-transaminases used in the present invention were obtained from Codexis Inc. under the reference numbers ATA-013, ATA-015, ATA-016, ATA-25, ATA-032, ATA-033, ATA-036, ATA-301, ATA-303, ATA-412, ATA-415, ATA-417 and ATA-436 (either part of the Codex® ATA Screening Kit or further genetically modified ω-transaminase variants, also obtained from Codexis Inc.). Such genetically modified ω-transaminases are described e.g. in U.S. Pat. Nos. 9,889,380, and 8,293,507, and 9,133, 445, EP patent number No EP2401366 and PCT application WO 2010/099501.

Coenzyme

Transaminases require the coenzyme pyridoxal-5'-phosphate (PLP). "Pyridoxal-phosphate," "PLP," "pyridoxal-5'-phosphate," "PYP," and "P5P" are used interchangeably herein to refer to the compound that acts as a coenzyme in transaminase reactions.

In some embodiments, pyridoxal phosphate is defined by the structure 1-(4'-formyl-3'-hydroxy-2'-methyl-5'-pyridyl) methoxyphosphonic acid, CAS number [54-47-7], pyridoxal-5'-phosphate can be produced in vivo by phosphorylation and oxidation of pyridoxol (also known as Vitamin B6). In transamination reactions using transaminase enzymes, the amine group of the amino donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces a chiral amine and regenerates the coenzyme.

In some embodiments, the pyridoxal-5'-phosphate can be replaced by other members of the vitamin B6 family, including pyridoxine (PN), pyridoxal (PL), pyridoxamine (PM), and their phosphorylated counterparts, pyridoxine phosphate (PNP), and pyridoxamine phosphate (PMP).

Amine Donor

In the context of the present invention an amine donor is a molecule capable of providing an amino group to an amine acceptor using a transaminase, in particular an ω-transaminase. In a particular preferred embodiment the amine donor is an amine or amino acid.

In some embodiments, amino donors are molecules of the following general formula,

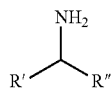

in which each of R' and R", when taken independently, is an alkyl, cycloalkyl, heterocycloalkyl, aryl, or heteroaryl, which is unsubstituted or substituted with one or more enzymatically non-inhibiting groups. R' can be the same or different from R" in structure or chirality. In some embodiments, R' and R", taken together, may form a ring that is unsubstituted, substituted, or fused to other rings. Typical amino donors that can be used include chiral and achiral amino acids, and chiral and achiral amines. Amino donors that can be used include, by way of example and not limitation, isopropylamine (2-aminopropane), β-alanine, alanine, in particular D,L-alanine, L-alanine or D-alanine, α-methylbenzylamine (α-MBA), glutamate, phenylalanine, glycine, 3-aminobutyrate, 2-aminobutane, γ-aminobutyrate and a salt, for instance a chloride, of any one thereof. In a preferred embodiment thereof, isopropylamine (2-aminopropane) is the amine donor.

In such an embodiment, the obtained ketone product will be acetone, phenylpyruvic acid or a salt thereof, pyruvic acid or a salt thereof, glyoxylic acid or a salt thereof, acetophenone, 2-ketoglutarate, 3-oxobutyrate, 2-butanone, 3-oxopyrrolidine (3-OP), 3-pyridylmethylketone (3-PMK), 3-oxobutyric acid ethyl ester (3-OBEE), 3-oxopentanoic acid methyl ester (3-OPME), N-1-Boc-3-oxopiperidinone and N-1-Boc-3-oxopyrrolidine (B3OP) or a salt, for instance a chloride, of any one thereof. In a preferred embodiment thereof, the obtained ketone product is acetone.

Enzymatic Reaction Conditions:

"Suitable reaction conditions" refer to those conditions in the transaminase catalyzed reaction solution (e.g., ranges of enzyme loading, substrate loading, cofactor loading, temperature, pH, buffers, co-solvents, etc.) under which the selected transaminase is capable of converting a substrate compound to a product compound (e.g., conversion of the compound of formula (IV), preferably (IV-a), to the compound of formula (III), preferably (III-a)). Exemplary "suitable reaction conditions" are provided in the present disclosure and illustrated by the Examples.

"Loading", such as in "compound loading" or "enzyme loading" or "cofactor loading" refers to the concentration or amount of a component in a reaction mixture at the start of the reaction.

"Substrate" in the context of the transaminase catalyzed reaction process refers to the compound or molecule acted on by the enzyme. For example, an exemplary substrate for the transaminase in the process disclosed herein is compound (IV).

"Product" in the context of the transaminase catalyzed reaction process refers to the compound or molecule resulting from the action of the enzyme. For example, an exemplary product for the transaminase in the process disclosed herein is compound (III).

In the context of the present invention, the transaminase reaction is enantioselective, i.e. produces the desired enantiomer in excess of the undesired enantiomer. In some embodiments, the desired enantiomer is formed in at least 70%, 80%, 85%, 90%, 91%, 92%, 93%, 94%, 95%, 96%, 97%, 98%, 99% or greater enantiomeric excess (ee).

In the present invention it is preferred that the amino acceptor is converted to the desired chiral amine compound in a conversion rate of more than 50%, or at least 60, 70, 80, 90, 95, 99, in particular 100%.

Substituent Definitions

Alkyl is defined as a radical or part of a radical as a straight or branch (one or, if desired and possible, more times) carbon chain, and is especially $C_1$-$C_7$-alkyl, preferably $C_1$-$C_6$-alkyl, more preferably $C_1$-$C_4$-alkyl.

The terms "$C_1$-$C_7$-", "$C_1$-$C_6$-" and "$C_1$-$C_4$-", respectively, define a moiety with up to and including maximally 7, especially up to and including maximally 6 and 4 respectively, carbon atoms, said moiety being branched (one or more times) or straight-chained and bound via a terminal or a non-terminal carbon.

Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$-alkoxy is preferred.

Alkanoyl is, for example, $C_2$-$C_8$-alkanoyl and is, for example, acetyl [—C(=O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$-alkyl and is in particular halo-$C_1$-$C_4$-alkyl, such as trifluoromethyl, 1,1,2-trifluoro-2-chloroethyl or chloromethyl. Preferred halo-$C_1$-$C_7$-alkyl is trifluoromethyl.

Alkenyl may be linear or branched alkyl containing a double bond and comprising preferably 2 to 12 carbon atoms, 2 to 10 carbon atoms being especially preferred. Particularly preferred is a linear $C_2$-$C_7$-alkenyl, more preferably $C_2$-$C_4$-alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$-alkyl and is especially $C_2$-$C_7$-alkylene or $C_2$-$C_7$-alkylene and, optionally, can be interrupted by one or more, e.g. up to three oxygen, NR14 or sulfur, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$alkoxy.

Alkenylene is a bivalent radical derived from $C_{2-7}$-alkenyl and can be interrupted by one or more, e.g. up to three oxygen, NR14 or sulfur, wherein R14 is alkyl, and is unsubstituted or substituted by one or more, e.g. up to three substitutents, preferably independently selected from the substituents mentioned above for alkylene.

Aryl being a radical or part of a radical is, for example $C_{6-10}$-aryl, and is preferably a mono- or polycyclic, especially monocyclic, bicyclic or tricyclic aryl moiety with 6 to 10 carbon atoms, such as phenyl, naphthyl or fluorenyl preferably phenyl, and which can be unsubstituted or substituted, by one or more substituents, independently selected from, e.g. $C_1$-$C_7$-alkyl, $C_1$-$C_7$-alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to an aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms, independently selected from nitrogen, oxygen, sulfur, S(=O)— or S—(=O)$_2$, and is unsubstituted or substituted by one or more, e.g. up to three substitutents, preferably independently selected from the group consisting of halo, $C_1$-$C_7$-alkyl, halo-$C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl. Heterocyclyl is preferably imizazolyl, pyrazolyl, oxazolyl, isoxazolyl, thiazolyl, isothiazolyl, pyridinyl, pyranyl, diazionyl, oxazinyl, thiazinyl, dioxinyl, dithiinyl, azepanyl, oxepanyl, thiepanyl, indolyl, isoindoly, quinolinyl, isoquinolinyl, benzazepinyl, carbazolyl, imidazolidinyl, pyrazolidinyl, oxazolidinyl, isoxazolinidyl, thiazolidy, dioxolanyl, dithiolanyl, furazanyl, oxadiazolyl, thiadiazolyl, dithiazolyl, tetrazolyl, piperidinyl, piperazinyl, morpholinyl, thiomorpholinyl, oxothiomorpholinyl, dioxothiomorpholinyl, dioxanyl, dithianyl, azepanyl, oxepanyl, thiepanyl, or benzo-fused variants thereof.

In heterocyclylalkyl, the heterocyclyl is preferably as just defined and is attached to an alkyl as defined for alkyl. Examples are imidazolylmethyl, pyridylmethyl or piperidinylmethyl.

Acetyl is —C(=O)$C_1$-$C_7$-alkyl, preferably —C(=O)Me.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$-alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$-aryl-$C_1$-$C_7$-alkylsulfenyl or (unsubstituted or substituted) $C_{6-10}$-arylsulfenyl, wherein if more than one substituent is present, e.g. one to four substitutents, the substituents are selected independently from nitro, halo, halo-$C_1$-$C_7$-alkyl and $C_1$-$C_7$-alkyloxy.

Imide refers to a (unsubstituted or substituted) functional group consisting of two acyl groups bound to nitrogen, preferably a cyclic group derived from dicarboxylic acids. Especially preferred is succinimidyl derived from succinic acid or phthalimidyl derived from phthalic acid. The imidyl group may be substituted by one or more substituents independently selected from for example, $C_1$-$C_7$-alkyl, $C_1$-$C_7$-alkoxy-$C_1$-$C_7$-alkyl, $C_1$-$C_7$-alkoxy or halo.

Azide refers to a group —N=N$^+$=N$^-$.

Silyl, as used herein, refers to a group according to the formula —SiR11R12R13, wherein R11, R12 and R13 are, independently of each other, $C_1$-$C_7$-alkyl, $C_6$-$C_{10}$-aryl or phenyl-$C_1$-$C_4$-alkyl. Preferred examples for R11, R12 and R13 are methyl, ethyl, isopropyl, tert-butyl, phenyl or phenyl-$C_{1-4}$-alkyl.

Salts

Salts are especially pharmaceutically acceptable salts or generally salts of any of the intermediates mentioned herein, except if salts are excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Nitrogen Protecting Groups

The term "nitrogen protecting group" (e.g. Ra in this disclosure) comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used e.g. in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis', fourth edition, Wiley, New Jersey, 2007, and "The Peptides"; volume 3 (editors: E. Gross and J. Meienhofer), Academic Press, London and New York 1981, and "Methoden der organischen Chemie" (Methods of Organic Chemistry), Houben Weyl, fourth edition, volume 15/I, Georg Thieme Verlag, Stuttgart 1974.

Preferred nitrogen protecting groups generally comprise: unsubstituted or substituted $C_1$-$C_6$-alkyl, preferably $C_1$-$C_4$-alkyl, more preferably $C_1$-$C_2$-alkyl, most preferably $C_1$-alkyl, unsubstituted or substituted $C_{2-4}$-alkenyl, wherein each $C_1$-$C_6$-alkyl and $C_{2-4}$-alkenyl is optionally mono-, di- or tri-substituted by trialkylsilyl-$C_1$-$C_7$-alkoxy (e.g. trimethylsilylethoxy), cycloalkyl, aryl, preferably phenyl, or a heterocyclic group, preferably pyrrolidinyl, wherein the cycloalkyl group, the aryl ring or the heterocyclic group is unsubstituted or substituted by one or more, e.g. two or three residues, e.g. selected from the group consisting of $C_1$-$C_7$-alkyl, hydroxy, $C_1$-$C_7$-alkoxy, $C_2$-$C_8$-alkanoyl-m, halogen, nitro, cyano, and $CF_3$; aryl-$C_1$-$C_2$-alkoxycarbonyl (preferably phenyl-$C_1$-$C_2$-alkoxycarbonyl e.g. benzyloxycarbonyl); $C_{1-10}$-alkenyloxycarbonyl; $C_{1-6}$-alkylcarbonyl (e.g. acetyl or pivaloyl); $C_{6-10}$-arylcarbonyl (e.g. benzoyl); $C_{1-6}$-alkoxycarbonyl (e.g. tert-butoxycarbonyl); $C_{6-10}$-aryl-$C_{1-6}$-alkoxycarbonyl; allyl or cinnamyl; sulfonyl or sulfenyl; a succinimidyl group, substituted silyl, e.g. triarylsilyl or trialkylsilyl (e.g. triethylsilyl).

Examples of preferred nitrogen protecting groups are acetyl, benzoyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert-butyldimethylsilyl (TBDMS), triethylsilyl (TES), triisopropylsilyl (TIPS), trimethylsilyethoxymethyl (SEM), tert-butoxycarbonyl (Boc), tert-butyl, 1-methyl-1,1-dimethylbenzyl, (phenyl)methylbenzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), tert-butoxycarbonyl (Boc), pyrrolidinylmethyl and pivaloyl.

Examples of more preferred nitrogen protecting groups are, pivaloyl, pyrrolidinylmethyl, tert-butoxycarbonyl, benzyl and silyl groups, particularly silyl groups according to the formula SiR11R12R13 group, wherein R11, R12 and R13 are, independently of each other, $C_1$-$C_7$-alkyl, $C_6$-$C_{10}$-aryl or phenyl-$C_{1-}C_4$-alkyl. Preferred examples for R11, R12 and R13 are methyl, ethyl, isopropyl, tert-butyl and phenyl.

Examples of most preferred nitrogen protecting groups are tert-butoxycarbonyl (Boc), benzoyl, styryl, 1-butenyl, benzyl, p-methoxybenzyl (PMB) and pyrrolidinylmethyl, in particular pivaloyl and tert-butoxycarbonyl (Boc).

In one embodiment the term nitrogen protecting group refers to a group which is selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O) or S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$;

$C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl, and silyl, wherein each silyl group is a SiR11R12R13 group, wherein R11, R12 and R13 are, independently of each other, $C_1$-$C_7$-alkyl, $C_6$-$C_{10}$-aryl or phenyl-$C_{1-}C_4$-alkyl.

Generally, in the present application the term "nitrogen protecting group" comprises any group which is capable of reversibly protecting an amino functionality.

If an embodiment requires the removal of the nitrogen protecting group, as defined above, the removal usually can be carried out by using known methods. e.g. as described in the references cited above. Preferably, the nitrogen protecting group, as defined above, is removed by using acidic or basic conditions. Examples for acidic conditions are hydrochloric acid, trifluoroacetic acid, sulphuric acid. Examples of basic conditions are lithium hydroxide, sodium ethoxide. Nucleophiles such as sodium borohydride can be used. In the case of N-benzyl as amino protecting group it can be removed by hydrogenation or by the use of some suitable oxidizing agents, e.g. ceric ammonium nitrate (CAN) or 2,3-dichloro-5,6-dicyano-p-benzoquinone (DDQ).

Carboxyl Protecting Groups

A carboxyl protecting group (e.g. R in this disclosure) can be any group known in the art, especially $C_1$-$C_6$-alkyl, e.g. ethyl, methyl, allyl or tert-butyl, or $C_6$-$C_{10}$-aryl-$C_1$-$C_6$-alkyl, e.g. benzyl, or a silyl group SiR11R12R13, wherein R11, R12, and R13 are, independently of each other, $C_1$-$C_7$-alkyl, $C_6$-$C_{10}$-aryl or phenyl-$C_1$-$C_4$-alkyl. Preferred examples for R11, R12 and R13 are methyl, ethyl, isopropyl, tert-butyl, phenyl or phenyl-$C_{1-4}$-alkyl. The carboxyl protecting groups themselves, their introduction reactions, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosauren, Peptide, Proteine" (*Amino acids, peptides, proteins*), Verlag Chemie, Weinheim, Deerfield Beach, and Basel 1982, and in Jochen Lehmann, "Chemie der Kohlen hydrate: Monosaccharide and Derivate" (*Chemistry of carbohydrates: monosaccharides and derivatives*), Georg Thieme Verlag, Stuttgart 1974.

For example, an $C_1$-$C_6$-alkyl, e.g. ethyl, protecting group R* or Ra can be removed by hydrolysis, e.g. in the presence of a base, such as an alkaline metal hydroxide, e.g. lithium hydroxide, in the presence of an appropriate solvent, e.g. a cyclic ether, such as tetrahydrofuran, and water, e.g. at a temperature in the range from 0 to 50° C., such as from 10 to 30° C.

Generally this implies that wherever the term "protecting group" is used in the present specification, a protecting group is only used as such if it is removed for the next to follow product—if it remains, the protecting group is becoming a substituent. Thus, alkyl, such as ethyl, if removed, is a protecting group, if it remains, it becomes a permanent moiety.

Where protecting groups are mentioned, it is their characteristic that, in contrast to groups that remain in a molecule, they are cleaved off in a following reaction step; therefore alkyl, such as ethyl, as protecting group, based on this function, is to be distinguished from alkyl, such as ethyl, that is to stay in a reaction product.

EMBODIMENTS

The following sections describe in more detail, as necessary the individual process steps as laid out in SCHEMES 1 to 4 above and as depicted in the claims.

Reactions According to SCHEME 1 and SCHEME 1-a— Step c

In the first aspect of the present invention, all embodiments necessarily always comprise the process step c of SCHEME 1 and SCHEME 1-a, respectively:

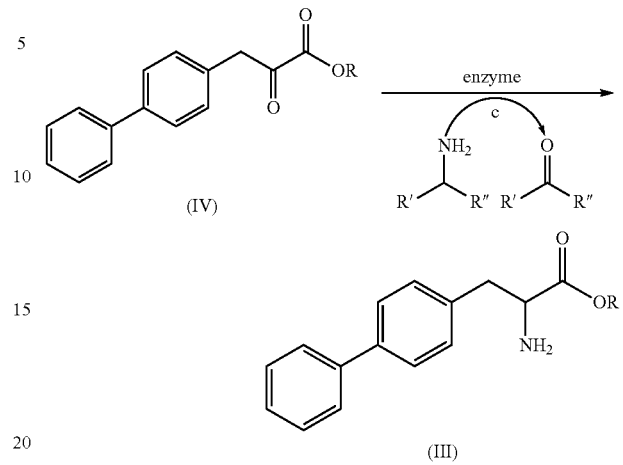

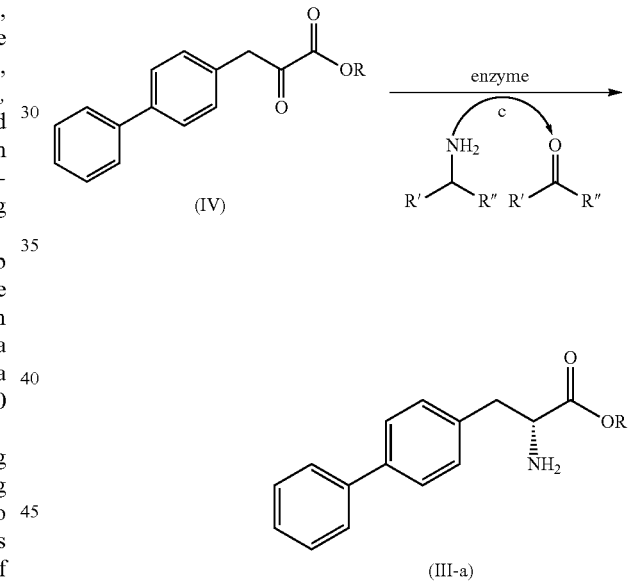

wherein in both SCHEME 1 and SCHEME 1-a, R is hydrogen or a carboxyl protecting group.

Accordingly, in this aspect, the present invention relates to a process for preparing a compound of formula (III), or a salt thereof

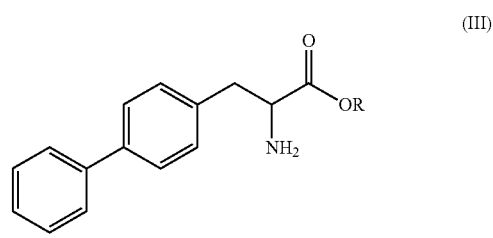

preferably a compound of formula (III-a), or a salt thereof

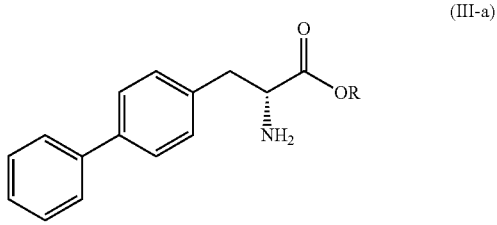

(III-a)

wherein in both formulae R is hydrogen or a carboxyl protecting group,
comprising converting a compound of formula (IV), or a salt thereof,

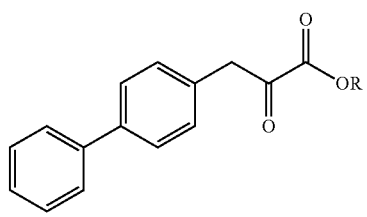

(IV)

wherein R is hydrogen or a carboxyl protecting group,
into the compound of formula (III) by bringing it in contact with an (R)-selective ω-transaminase in the presence of an amine donor, wherein the conversion rate from the compound of formula (IV) to the compound of formula (III), preferably to the compound of formula (III-a), is more than 50%.

In one embodiment, the reaction is carried out in the presence of a coenzyme.

In one embodiment thereof, R is hydrogen or $C_1$-$C_6$-alkyl, for example ethyl. In particular, R is hydrogen.

In one embodiment, the amine donor is of the formula

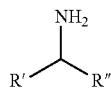

in which each of R' and R", when taken independently, is an alkyl, cycloalkyl, heterocycloalkyl, aryl, or heteroaryl, which is unsubstituted or substituted with one or more enzymatically non-inhibiting groups. R' can be the same or different from R" in structure or chirality. In some embodiments, R' and R", taken together, may form a ring.

In one embodiment thereof, the amine donor is an achiral amine donor. In particular the achiral amine donor is selected from the group consisting of achiral $C_1$-$C_7$-alkylamine, achiral $C_3$-$C_8$-cycloalkylamine, achiral $C_6$-$C_{10}$-aryl-$C_1$-$C_7$-alkylamine, achiral $C_1$-$C_7$-alkyldiamine, achiral amino-$C_1$-$C_7$-alkanoic acid, and achiral $C_6$-$C_{10}$-aryl-di($C_1$-$C_7$-alkylamine). In a particular embodiment, the achiral amine donor is isopropylamine (2-aminopropane), which can alternatively also be used as a suitable salt thereof.

In one embodiment, the co-enzyme used is pyridoxyl 5'-phosphate.

In one embodiment, the transamination reaction takes place in the presence of an (R)-selective ω-transaminase selected from ATA-013, ATA-015, ATA-016, ATA-025, ATA-032, ATA-033, ATA-036, ATA-301, ATA-303, ATA-412, ATA-415, ATA-417 or ATA-436, commercially available from Codexis, Inc., Redwood City, Calif., USA, an amine donor, e.g. isopropylamine (alternatively used as a suitable salt), and a co-enzyme, preferably pyridoxyl 5'-phosphate (PLP), in an appropriate solvent, e.g. aqueous dipotassium hydrogenphosphate buffer, preferably at pH 7 to 10, e.g. at pH 8 to 9, potentially achieved by adjustment of the pH value, e.g. by addition of isopropylamine, preferably at temperatures in the range from 20 to 60° C., e.g. at 20 to 50° C.

The conversion rate from the compound of formula (IV) to the compound of formula (III), preferably to the compound of formula (III-a), is more than 55%, at least about 60%, at least about 70%, at least about 80%, at least about 90%, at least about 95%, at least about 98%, or at least about 99%, or even 100%.

In some embodiments, the transaminase is capable of converting the substrate compound of formula (IV), in particular the compound 3-([1,1'-biphenyl]-4-yl)-2-oxopropanoic acid, to the product compound of formula (III) and (III-a), respectively, in particular compound (R)-3-([1,1'-biphenyl]-4-yl)-2-aminopropanoic acid, in enantiomeric excess of greater than 80%, 85%, 86%, 87%, 88%, 89%, 90%, 91%, 92%, 93%, 94%, 95%, 96%, 97%, 98%, 99%, 99.5% or greater over the corresponding compound of formula (III-b)

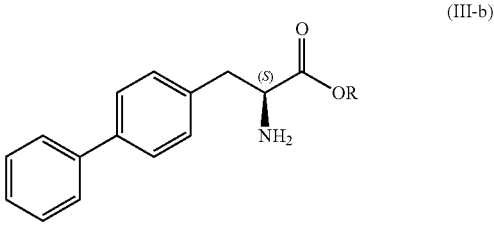

(III-b)

wherein R is selected from hydrogen and a carboxyl protecting group, e.g. $C_1$-$C_6$-alkyl, preferably hydrogen, under suitable reaction conditions.

In one embodiment, the transaminase reaction takes place in the presence of an (R)-selective ω-transaminase selected from ATA-013, ATA-015, ATA-016, ATA-025, ATA-032, ATA-033, ATA-036, ATA-301, ATA-303, ATA-412, ATA-415, ATA-417 or ATA-436 and achieves a conversion rate from the compound of formula (IV) to the compound of formula (III), preferably to the compound of formula (III-a), of more than 90% and produces the product compound of formula (III-a), in particular compound (R)-3-([1,1'-biphenyl]-4-yl)-2-aminopropanoic acid, in enantiomeric excess of greater than 85% or greater over the corresponding compound of formula (III-b).

In some embodiments, the transaminases used in the instant disclosure are capable of converting compound (IV) to compound (III-a) with increased tolerance for the presence of substrate under suitable reaction conditions. Thus, in some embodiments the transaminases are capable of converting the substrate compound (IV) to product compound (III-a), respectively, in the presence of a substrate loading concentration of at least about 1 g/L, about 5 g/L, about 10 g/L, about 20 g/L, about 30 g/L, about 40 g/L, about 50 g/L, about 70 g/L, about 80 g/L, or more. Such substrate loading still achieves a percent conversion of at least about 50%, at least about 60%, at least about 70%, at least about 80%, at least about 90%, at least about 95%, at least about 98%, or at least about 99%, or 100%, in a reaction time of about 120 h or less, about 96 h or less, about 72 h or less, about 48 h or less, about 36 h or less, or about 24 h or less, about 18 h or less or even 12 h or less, under suitable reaction conditions.

The suitable reaction conditions to achieve such conversion rates can be determined with respect to concentrations or amounts of transaminase, substrate, cofactor, buffer, co-solvent, pH, and/or conditions including temperature and reaction time, as further described below and in the Examples.

Detailed Methods of Using Transaminase Enzymes

For the foregoing processes, preferably the ω-transaminases obtainable from Codexis Inc. under the reference numbers ATA-013, ATA-015, ATA-016, ATA-25, ATA-032, ATA-033, ATA-036, ATA-301, ATA-303, ATA-412, ATA-415, ATA-417 and ATA-436 (either part of the Codex® ATA Screening Kit or further genetically modified ω-transaminase variants, also obtained from Codexis Inc.) were used. Such genetically modified ω-transaminases are described e.g. in U.S. Pat. Nos. 9,889,380, and 8,293,507, and 9,133,445, EP patent number No EP2401366 and PCT application WO 2010/099501.

In the embodiments herein and illustrated in the Examples, various ranges of suitable reaction conditions that can be used in the processes, including but not limited, to ranges of amino donor, pH, temperature, buffer, solvent system, substrate loading, enzyme (transaminase) loading, cofactor loading, pressure, and reaction time. Further suitable reaction conditions for carrying out the claimed transaminase process can be readily optimized in view of the guidance provided herein by routine experimentation that includes, but is not limited to, contacting the transaminase and substrate compound under experimental reaction conditions of concentration, pH, temperature, solvent conditions, and detecting the product compound.

In one embodiment of the invention, the transaminase uses isopropylamine (also referred to herein as "IPM") as amine donor. Suitable reaction conditions comprise the amine donor, in particular IPM, present at a concentration of at least about 0.1 to about 3.0 M, 0.2 to about 2.5 M, about 0.5 to about 2 M or about 1 to about 2 M. In some embodiments, the amino donor is present at a concentration of about 0.1, 0.2, 0.3, 0.4, 0.5, 0.6, 0.7, 0.8, 1.0, 1.5, 2.0, 2.5 or 3.0 M. Higher concentrations of amine donor, e.g., IPM, can be used to shift the equilibrium towards amine product formation.

Suitable reaction conditions also typically comprise a cofactor. In one embodiment, the cofactors is pyridoxal-5'-phosphate. In some embodiments, the cofactor PLP is present naturally in the cell extract and does not need to be supplemented. In other embodiments, the suitable reaction conditions comprise cofactor added to the enzyme reaction mixture, for example, when using partially purified, or purified transaminase enzyme. Suitable reaction conditions can comprise the presence of a cofactor preferably PLP, at a concentration of about 0.1 g/L to about 10 g/L, about 0.2 g/L to about 5 g/L, about 0.5 g/L to about 2.5 g/L. In some embodiments, the reaction conditions comprise a PLP concentration of about 0.1 g/L or less, 0.2 g/L or less, 0.5 g/L or less, 1 g/L or less, 2.5 g/L or less, 5 g/L or less, or 10 g/L or less. In some embodiments, the cofactor can be added either at the beginning of the reaction and/or additional cofactor is added during the reaction.

The concentration of the substrate compound of formula (IV) in the reaction mixture can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 100 g/L, 1 to about 90 g/L, 5 to about 80 g/L, about 10 to about 70 g/L, 20 to about 60 g/L or about 30 to about 50 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, or at least about 80 g/L.

Suitable reaction conditions comprise a transaminase concentration of about 0.01 to about 50 g/L; about 0.05 to about 50 g/L; about 0.1 to about 40 g/L; about 1 to about 40 g/L; about 2 to about 40 g/L; about 5 to about 40 g/L; about 5 to about 30 g/L; about 0.1 to about 10 g/L; about 0.5 to about 10 g/L; about 1 to about 10 g/L; about 0.1 to about 5 g/L; about 0.5 to about 5 g/L; or about 0.1 to about 2 g/L. In some embodiments, the transaminase concentration is at about 0.01, 0.05, 0.1, 0.2, 0.5, 1, 2, 5, 10, 15, 20, 25, 30, 35, 40, or 50 g/L.

During the course of the transamination reactions, the pH of the reaction mixture may change. The pH of the reaction mixture may be maintained at a desired pH or within a desired pH range. This may be done by the addition of an acid or a base, before and/or during the course of the reaction. Alternatively, the pH may be controlled by using a buffer. In some embodiments, the suitable reaction conditions comprise a solution pH comprise a pH from about 6 to about 12, pH from about 7 to about 11, pH from about 7 to about 9, pH from about 8 to about 10, pH from about 7 to about 9, or pH from about 8 to about 9. In some embodiments, the reaction conditions comprise a solution pH of about 6, 6.5, 7, 7.5, 8, 8.5, 9, 9.5, 10.0 10.5, 11, 11.5 or 12.

Accordingly, in some embodiments, the reaction condition comprises a buffer. Suitable buffers to maintain desired pH ranges are known in the art and include, by way of example and not limitation, borate, carbonate, phosphate, triethanolamine buffer, and the like. In some embodiments, the buffer is borate. In some embodiments of the process, the suitable reaction conditions comprise a buffer solution of phosphate, where the phosphate concentration is from about 0.001 to about 0.4 M, 0.01 to about 0.2 M, 0.05 to about 0.1 M, or about 0.05 to about 0.1 M. In some embodiments, the reaction condition comprises a phosphate concentration of about 0.01, 0.02, 0.03, 0.04, 0.05, 0.07, 0.08, 0.09, 0.1, 0.12, 0.14, 0.16, 0.18, 0.2, 0.3, or 0.4 M. In some embodiments, the reaction conditions comprise water as a suitable solvent with no buffer present.

In the embodiments of the transamination process, a suitable temperature can be used for the reaction conditions, for example, taking into consideration the increase in reaction rate at higher temperatures, and the activity of the enzyme during the reaction time period. Accordingly, in some embodiments, the suitable reaction conditions comprise a temperature of about 10° C. to about 70° C., about 10° C. to about 65° C., about 15° C. to about 60° C., about 20° C. to about 60° C., about 20° C. to about 55° C., about 30° C. to about 55° C., or about 40° C. to about 50° C. In some embodiments, the suitable reaction conditions comprise a temperature of about 10° C., 15° C., 20° C., 25° C., 30° C., 35° C., 40° C., 45° C., 50° C., 55° C., 60° C., 65° C., or 70° C. In some embodiments, the temperature during the enzymatic reaction can be maintained at a temperature throughout the course of the reaction. In some embodiments, the temperature during the enzymatic reaction can be adjusted over a temperature profile during the course of the reaction.

The processes of the disclosure are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the transaminase processes are generally carried out in an aqueous co-solvent system comprising an organic solvent (e.g., ethanol, isopropanol (IPA), dimethyl sulfoxide (DMSO), ethyl acetate, butyl acetate, 1-octanol, heptane, octane, methyl tert-butyl ether (MTBE), toluene, and the like), ionic or polar solvents (e.g., 1-ethyl-4-methylimidazolium tetrafluoroborate, 1-butyl-3-methylimidazolium tetrafluoroborate, 1-butyl-3-methylimidazolium hexafluorophosphate, glycerol, polyethylene glycol, and the like). In some embodiments, the co-solvent can be a polar solvent, such as a polyol, dimethylsulfoxide, DMSO, or lower alcohol. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the transaminase enzyme under the reaction conditions. Appropriate co-solvent systems can be readily identified by measuring the enzymatic activity of the specified transaminase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises a polyol solvent, particularly glycols. Examples of suitable polyol solvents include, by way of example and not limitation, polyethylene glycol, polyethylene glycol methyl ether, diethylene glycol dimethyl ether, triethylene glycol dimethyl ether, and polypropylene glycol. In some embodiments, the aqueous co-solvent comprises polyethylene glycol, which is available in different molecular weights. Particularly useful are lower molecular weight glycols, such as PEG200 to PEG600. Accordingly, in some embodiments, the aqueous co-solvent comprises PEG200 of about 1% to about 40% v/v; about 1% to about 40% v/v; about 2% to about 40% v/v; about 5% to about 40% v/v; 2% to about 30% v/v; 5% to about 30% v/v; 1 to about 20% v/v; about 2% to about 20% v/v; about 5% to about 20% v/v; about 1% to about 10% v/v; about 2% to about 10% v/v. In some embodiments, the suitable reaction conditions comprises an aqueous co-solvent comprising PEG200 at about 1%, 2%, 5%, 10%, 15%, 20%; 25%; 30%; 35%; 35% or about 40% v/v. Preferably no co-solvent is used.

In some embodiments of the process, the suitable reaction conditions comprise an aqueous co-solvent, where the co-solvent comprises DMSO at about 1% to about 80% (v/v), about 1 to about 70% (v/v), about 2% to about 60% (v/v), about 5% to about 40% (v/v), 10% to about 40% (v/v), 10% to about 30% (v/v), or about 10% to about 20% (v/v). In some embodiments of the process, the suitable reaction conditions comprise an aqueous co-solvent comprising DMSO at least about 1%, 5%, 10%, 15%, 20%, 25%, 30%, 35%, 40%, 45%, 50%, 55%, 60%, 65%, 70%, 75%, or 80% (v/v).

In some embodiments, the reaction mixture might also contain surfactants.

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent.

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the transaminase, and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase.

The transamination reaction is generally allowed to proceed until further conversion of ketone substrate to amine product does not change significantly with reaction time, e.g., less than 10% of substrate being converted, or less than 5% of substrate being converted. In some embodiments, the reaction is allowed to proceed until there is complete or near complete conversion of substrate ketone to product amine. Transformation of substrate to product can be monitored using known methods by detecting substrate and/or product. Suitable methods include gas chromatography, HPLC, and the like. Conversion yields of the chiral amine product generated in the reaction mixture are generally greater than about 50%, may also be greater than about 60%, may also be greater than about 70%, may also be greater than about 80%, may also be greater than 90%, and are often greater than about 97%.

Generally, the transamination reaction will proceed for a reaction time of about 120 h or less, about 96 h or less, about 72 h or less, about 48 h or less, about 36 h or less, about 24 h or less, about 18 h or less, or about 12 h or less, under suitable reaction conditions.

In some embodiments, the methods for preparing compounds of formula (III) and (III-a) using a transaminase under suitable reaction conditions results in at least about 90%, 91%, 92%, 93%, 94%, 95%, 96%, 97%, 98%, 99% or greater conversion of ketone substrate, e.g., compound of formula (IV), respectively, to the amine product compound, e.g., compound of formula (III) and (III-a), respectively, in about 48 h or less, in about 36 h or less, in about 24 h or less, in about 18 h or less, or even less time.

In a further embodiment, the suitable reaction conditions comprise an initial substrate loading to the reaction solution which is then contacted with the transaminase. This reaction solution is the further supplemented with additional substrate of compound as a continuous addition over time at a rate of at least about 1 g/L/h, at least about 2 g/L/h, at least about 4 g/L/h, at least about 6 g/L/h, or higher. Thus, according to these suitable reaction conditions transaminase is added to a solution having an initial substrate loading of at least about 20 g/L, 30 g/L, or 40 g/L. This addition of transaminase is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the method, the suitable reaction conditions comprise addition of the transaminase to a solution having an initial substrate loading of at least about 20 g/L, 30 g/L, or 40 g/L followed by addition of further substrate to the solution at a rate of about 2 g/Uh, 4 g/Uh, or 6 g/Uh until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of ketone substrate to amine product of at least about 90%, 91%, 92%, 93%, 94%, 95%, 96%, 97%, 98%, 99% or greater. In some embodiments of this method, the further substrate added is in a solution comprising isopropylamine or isopropylamine acetate at a concentration of at least about 0.5 M, at least about 1.0 M, at least about 2.5 M, at least about 5.0 M, at least about 7.5 M, at least about 10.0 M.

In some embodiments of the processes, the transamination reaction can comprise the following suitable reaction conditions: (a) substrate loading at about 5 g/L to 100 g/L; (b) about 0.1 to 50 g/L of transaminase; (c) about 0.1 to 4 M of isopropylamine (IPM); (d) about 0.1 to 10 g/L of pyridoxal phosphate (PLP) cofactor; (e) pH of about 6 to 10; and (f) temperature of about 30 to 60° C.

In some embodiments of the processes, the transamination reaction can comprise the following suitable reaction conditions: (a) substrate loading at about 10 to about 80 g/L; (b) about 0.5 to 25 g/L of transaminase; (c) about 0.1 to 2 M of isopropylamine (IPM); (d) about 0.1 to 1 g/L of pyridoxal phosphate (PLP) cofactor; (e) pH of about 8 to 10; (f) temperature of about 40 to 55° C., and (g) reaction times of 18 hr to 36 hr.

In some embodiments of the processes, the transamination reaction can comprise the following suitable reaction conditions: (a) substrate loading of about 25 to about 80 g/L; (b) about 0.5 to 10 g/L of transaminase; (c) about 0.1 to 2 M of isopropylamine (IPM); (d) about 0.1 to 1 g/L of pyridoxal phosphate (PLP) cofactor; (e) about 0.005 to about 0.1 M of borate (or comparable) buffer; (f) pH of about 8 to 10; and (g) temperature of about 40 to 55° C.

In some embodiments, additional reaction components or additional techniques are carried out to supplement the reaction conditions. These can include taking measures to stabilize or prevent inactivation of the enzyme, reduce product inhibition, or shift reaction equilibrium to product formation.

Accordingly, in some embodiments of the process for preparing an amine, such as a chiral amine, additional quantities of the amino acceptor can be added (up to saturation) and/or the amino acceptor (ketone) formed can be continuously removed from the reaction mixture. For example, a solvent bridge or a two phase co-solvent system can be used to move the amine product to an extraction solution, and thereby reduce inhibition by amine product and also shift the equilibrium towards product formation (see, e.g., Yun and Kim, Biosci. Biotechnol. Biochem. 2008, 72, 3030-3033).

In some embodiments, where the choice of the amino donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas. In some embodiments, the amino donor used in the process is isopropylamine (IPM), which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal.

In further embodiments, any of the above described processes for the conversion of substrate compound to product compound can further comprise one or more steps selected from: extraction; isolation; purification; and crystallization of product compound. Methods, techniques, and protocols for extracting, isolating, purifying, and/or crystallizing the product amine from biocatalytic reaction mixtures produced by the above disclosed methods are known to the ordinary artisan and/or accessed through routine experimentation.

Reactions According to SCHEME 1 and SCHEME 1-a—
Steps a and b

In the first aspect of the present invention, the mandatory process step c of SCHEME 1 and SCHEME 1-a, respectively, is preceded by reaction steps b and a. Accordingly, in a further embodiment, the starting material of the transaminase reaction, namely the compound of formula (IV), or a salt thereof,

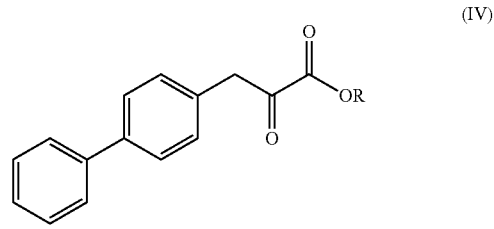

(IV)

wherein R is hydrogen or a carboxyl protecting group, is obtained by a process comprising hydrolysis of a compound of formula (V),

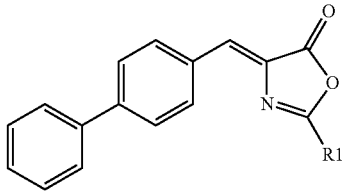

wherein R1 is optionally substituted $C_1$-$C_7$-alkyl, $C_6$-$C_{10}$-aryl or $C_6$-$C_{10}$-aryl-$C_1$-$C_7$-alkyl, under acidic or basic conditions, to obtain a compound of formula (IV) wherein R is hydrogen, and optionally introduction of a carboxyl protecting group R. Said process step is then followed by the aforementioned transaminase reaction to deliver the compound of formula (III) and (III-a), respectively.

In one embodiment thereof, R1 is methyl, benzyl or phenyl.

Appropriate reaction conditions are well-known in the art. The reaction preferably takes place in the presence of an aqueous inorganic acid, e.g. a hydrohalic acid, such as hydrochloric acid, or sulfuric acid, in an appropriate solvent or solvent mixture, e.g. a carboxylic acid, such as acetic acid, and/or water, at preferred temperatures in the range from 50° C. to the reflux temperature of the reaction mixture, e.g. from 70 to 100° C.; or an aqueous inorganic base, e.g. an alkali hydroxide, such as sodium hydroxide, in an appropriate solvent or solvent mixture, e.g. water, at preferred temperatures in the range from 50° C. to the reflux temperature of the reaction mixture, e.g. from 70 to 100° C.

In further embodiment of the present invention,

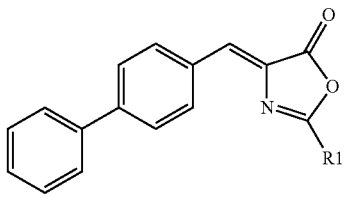

wherein R1 is optionally substituted $C_1$-$C_7$-alkyl, $C_6$-$C_{10}$-aryl or $C_6$-$C_{10}$-aryl-$C_1$-$C_7$-alkyl, can be obtained by a process comprising a reaction of the compound of formula (VI)

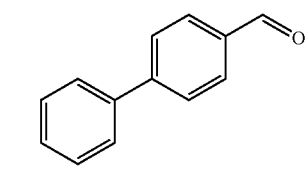

with a compound of formula (VII), or a salt thereof

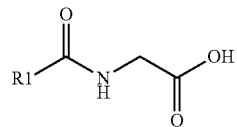

wherein R1 is optionally substituted $C_1$-$C_7$-alkyl, $C_6$-$C_{10}$-aryl or $C_6$-$C_{10}$-aryl-$C_1$-$C_7$-alkyl.

Appropriate reaction conditions are well-known in the art (e.g. Erlenmeyer azlactone synthesis). The reaction preferably takes place in the presence of an activating agent, such as acetic anhydride, optionally in an appropriate solvent, e.g. toluene or an ether, such as tetrahydrofuran, and an inorganic base, e.g. an alkali acetate, such as sodium acetate, at preferred temperatures in the range from 50° C. to the reflux temperature of the reaction mixture, e.g. from 70 to 100° C.

Alternative methods for the preparation of the compound of formula (IV) are described in U.S. Pat. Nos. 4,721,726, 4,447,644, Tetrahedron 2012, 68, 3708-3716, *Org. Biomol. Chem.* 2004, 2, 1864-1871, or WO 2011/035569 (step a).

Reactions According to SCHEME 2 and SCHEME 2-a, SCHEME 2* and SCHEME 2*-a, and SCHEME 2 and SCHEME 2-a:

In the first aspect of the present invention, the compound of formula (III) and (III-a), respectively,

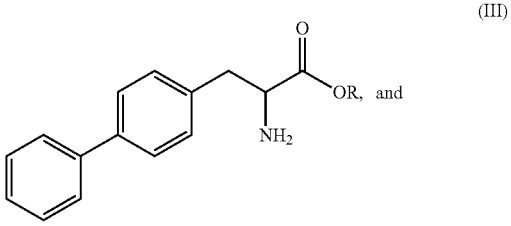

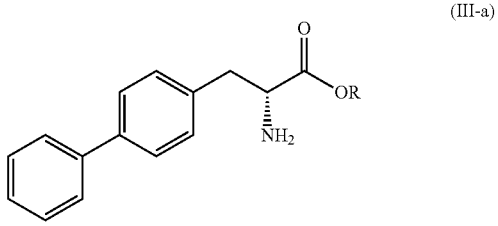

wherein R is hydrogen or a carboxyl protecting group, obtained as a result of the transaminase reaction, is then converted in a subsequent step to a compound of formula (I) and (I-a), respectively, or salts thereof

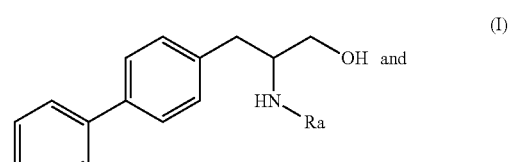

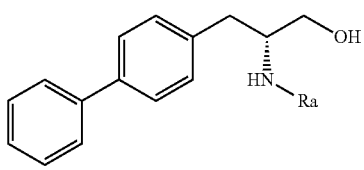

(I-a)

wherein Ra is a nitrogen protecting group, by a reaction sequence as depicted in any one of SCHEME 2 and SCHEME 2-a, SCHEME 2* and SCHEME 2*-a, and SCHEME 2 and SCHEME 2-a, respectively.

In a first embodiment thereof, according to SCHEME 2 and SCHEME 2-a, step d, the obtained compound of formula (III), or a salt thereof

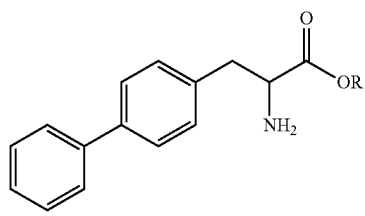

(III)

preferably a compound of formula (III-a), or a salt thereof

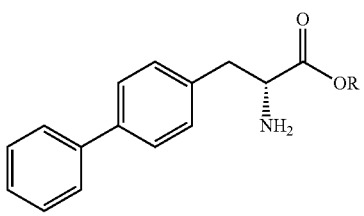

(III-a)

wherein in both formulae R is hydrogen or a carboxyl protecting group, is converted into a compound of formula (II), or a salt thereof

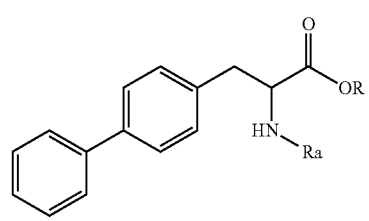

(II)

preferably a compound of formula (II-a), or a salt thereof

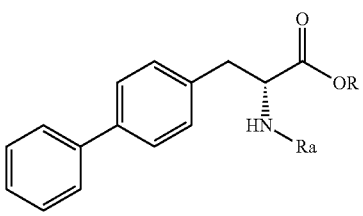

(II-a)

wherein in both formulae R is hydrogen or a carboxyl protecting group, and Ra is a nitrogen protecting group, by a process comprising introduction of a nitrogen protecting group Ra.

In one embodiment thereof, R is hydrogen.

In one embodiment, the compound of formula (II-a) is of formula (II-a)*

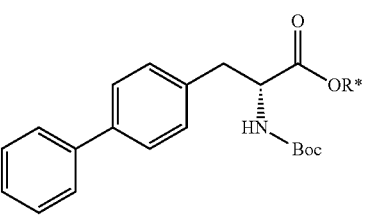

(II-a)

wherein R is hydrogen or a carboxyl protecting group, preferably hydrogen, which is obtained by reaction of the compound of formula (III-a) with di-tert-butyl dicarbonate.

In one embodiment thereof, the reaction can take place under customary conditions and using a reagent known in the art that introduces an amino protecting group, such as an anhydride, e.g. for the introduction of the preferred tert-butoxycarbonyl (Boc) group, preferably the reaction uses di-tert-butyl dicarbonate (Boc anhydride) as reagent and is performed in the presence of a base such as an inorganic base, e.g. an alkali hydroxide, such as sodium hydroxide, in an appropriate solvent or solvent mixture, e.g. in a mixture of an organic solvent, such as tetrahydrofuran, and water, e.g. at ambient temperatures, such as from 20° C. to 40° C.; or with an organic base, e.g. triethylamine, in an appropriate solvent or solvent mixture, such as an alcohol, e.g. methanol, an ether, e.g. tetrahydrofuran or 1,4-dioxane, or dichloromethane at temperatures e.g. in the range of from −20° C. to the reflux temperature of the reaction mixture, e.g. from 0 to 30° C.

In a further embodiment thereof, according to SCHEME 2 and SCHEME 2-a, step e, the now obtained compound of formula (II), or a salt thereof

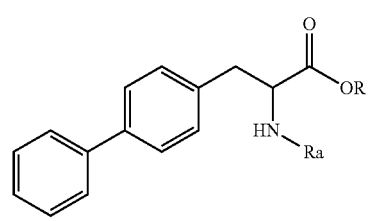

(II)

preferably a compound of formula (II-a), or a salt thereof

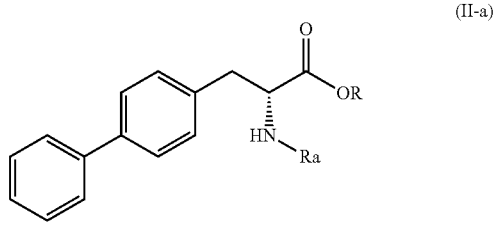

wherein in both formulae R is hydrogen or a carboxyl protecting group, and Ra is a nitrogen protecting group, is converted into a compound of formula (I), or a salt thereof

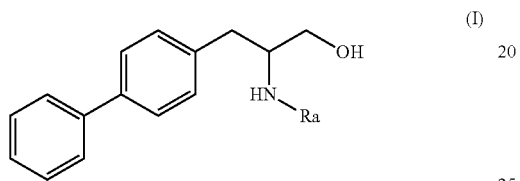

preferably a compound of formula (I-a), or a salt thereof

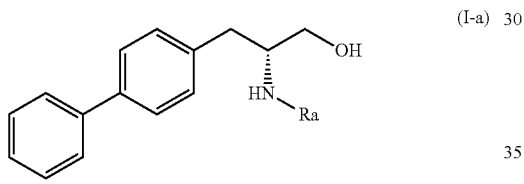

wherein in both formulae Ra is a nitrogen protecting group, by a process comprising reduction of the compound of formula (II) in the presence of a reducing agent.

In one embodiment, when in the compound of formula (II) and (II-a), respectively, R is hydrogen, i.e. the reaction is a reduction of the free carboxylic group, an activating agent is used, such as an acyl chloride, e.g. pivaloyl chloride, or a chloroformate, e.g. isobutyl chloroformate, in the presence of an organic base, e.g. an amine base, such as N-methylmorpholine, followed by use of complex hydrides, such as an alkali metal borohydride, e.g. sodium borohydride, or an alkali metal aluminium hydride, such as lithium aluminium hydride. The reaction preferably takes place in a customary solvent or solvent mixture, e.g. an ether, such as tetrahydrofuran, or a mixture of an ether, such as tetrahydrofuran, and water, at appropriate temperatures, e.g. in the range from −40 to 40° C., e.g. from −20 to 25° C. Alternatively, diisobutylaluminium hydride, borane, Red-Al (sodium bis(2-methoxyethoxy)-aluminum hydride) or sodium tetrahydroborate in combination with iodine may be used in an appropriate solvent, such as an ether, e.g. tetrahydrofuran, at low temperatures, e.g. in the range from −100 to 0° C., e.g. at −78° C.

In an alternative embodiment, when in the compound of formula (II) and (II-a), respectively, R is a carboxyl protecting group, i.e. the reaction is a reduction of the esterified carboxylic group, complex hydrides are used, such as an alkali metal borohydride, e.g. sodium borohydride, lithium borohydride, potassium borohydride, or an alkali metal aluminium hydride, such as lithium aluminium hydride, or borane or borane complexes, or alkyl aluminium hydrides, such as DIBAL. The reaction preferably takes place in a customary solvent or solvent mixture, e.g. an ether, such as tetrahydrofuran, or a mixture of an ether, such as tetrahydrofuran, and an alcohol, such as methanol, optionally in the presence of an additive, e.g. an alkali halide, such as lithium chloride, at appropriate temperatures, e.g. in the range from −20 to 40° C., e.g. from 0 to 25° C. In cases were R is an alkyl or aryl group, reduction can also be achieved by hydrogenation in the presence of appropriate metal catalysts such as Pd/C.

In a preferred embodiment, the compound of formula (II-a)*

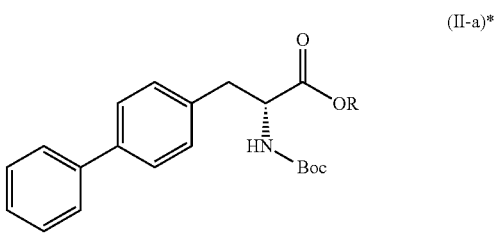

wherein R is hydrogen, is activated by reaction with isobutyl chloroformate in the presence of N-methylmorpholine, followed by reduction using sodium borohydride to obtain the compound of formula (I-a)*

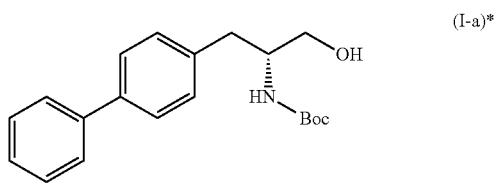 [SMILES: CC(C)(C)OC(=O)N[C@@H](CO)Cc1ccc(-c2ccccc2)cc1]

In a second embodiment thereof, according to SCHEME 2* and SCHEME 2*-a, step d, the obtained compound of formula (III), or a salt thereof

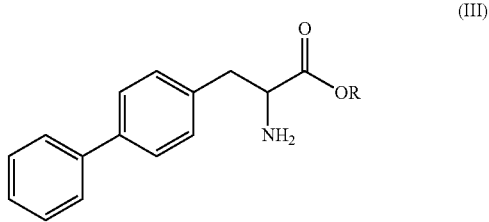

preferably a compound of formula (III-a), or a salt thereof

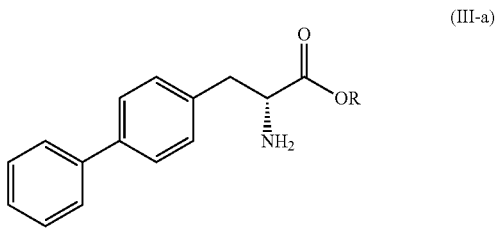

wherein in both formulae R is hydrogen, is first converted into a compound of formula (III), or a salt thereof

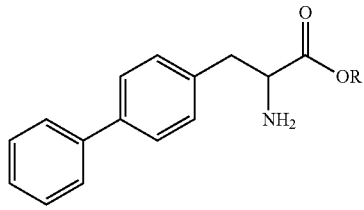

(III)

preferably a compound of formula (III-a), or a salt thereof

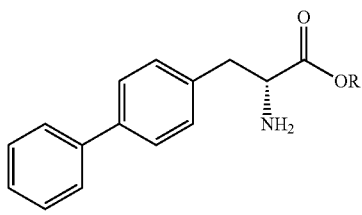

(III-a)

wherein in both formulae R is $C_1$-$C_7$-alkyl, $C_6$-$C_{10}$-aryl or $C_6$-$C_{10}$-aryl-$C_1$-$C_7$-alkyl, by a process comprising reaction with an alcohol R—OH wherein R optionally substituted is $C_1$-$C_7$-alkyl, $C_6$-$C_{10}$-aryl or $C_6$-$C_{10}$-aryl-$C_1$-$C_7$-alkyl (esterification reaction), which is then subsequently converted into a compound of formula (II), or a salt thereof

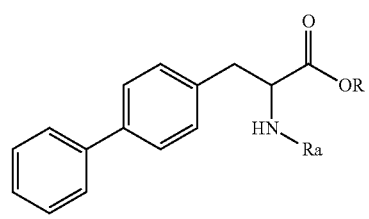

(II)

preferably a compound of formula (II-a), or a salt thereof

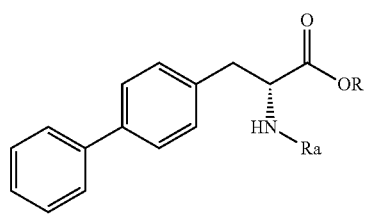

(II-a)

wherein in both formulae R is $C_1$-$C_7$alkyl, $C_6$-$C_{10}$-aryl or $C_6$-$C_{10}$-aryl-$C_1$-$C_7$-alkyl, and Ra is a nitrogen protecting group, by a process comprising introduction of a nitrogen protecting group Ra.

In one embodiment, the esterification reaction uses methanol, and accordingly R is methyl.

In another embodiment, the nitrogen protecting group is tert-butoxycarbonyl (Boc) group, and therefore, the second reaction step uses di-tert-butyl dicarbonate.

In one embodiment, the esterification reaction can take place under customary conditions using the desired alcohol R—OH wherein R is optionally substituted $C_1$-$C_7$-alkyl, $C_6$-$C_{10}$-aryl or $C_5$-$C_{10}$-aryl-$C_1$-$C_7$-alkyl, preferably unsubstituted $C_1$-$C_7$-alkyl, $C_6$-$C_{10}$-aryl or $C_6$-$C_{10}$-aryl-$C_1$-$C_7$-alkyl, preferably $C_1$-$C_7$-alkyl, such as methyl, ethyl, phenethyl or benzyl, more preferably methyl, in the presence of an activating agent, e.g. an agent to transform the free carboxylic acid into an acyl halide or acid anhydride, before performing the actual esterification reaction. Suitable reagents for formation of an acyl halide are for example selected from thionyl chloride, thionyl bromide, $PCl_3$, $PCl_5$, oxalyl chloride, $Me_2C=C(Cl)NMe_2$, PhCOCl, $PBr_3$, $PBr_5$, $Ph_3PBr_2$, oxalyl bromide or $Me_2C=C(Br)NMe_2$. The reaction preferably takes place in a customary solvent, such as the respective alcohol R—OH as defined above, preferably methanol or ethanol, and at appropriate temperatures, e.g. in the range from 0 to 100° C., e.g. from 10 to 90° C.

In another embodiment, the second step, namely the introduction of the nitrogen protecting group into the compound of formula (III) and (III-a), respectively, wherein R is $C_1$-$C_7$-alkyl, $C_6$-$C_{10}$-aryl or $C_6$-$C_{10}$-aryl-$C_1$-$C_7$-alkyl, can be performed as described above: the reaction can take place under customary conditions and using a reagent known in the art that introduces an amino protecting group, such as an anhydride, e.g. for the introduction of the preferred tert-butoxycarbonyl (Boc) group, preferably the reaction uses di-tert-butyl dicarbonate (Boc anhydride) as reagent and is performed in the presence of a base such as an inorganic base, e.g. an alkali hydroxide, such as sodium hydroxide, in an appropriate solvent or solvent mixture, e.g. in a mixture of an organic solvent, such as tetrahydrofuran, or tetrahydrofuran and water, e.g. at ambient temperatures, such as from 20° C. to 40° C.; or with an organic base, e.g. triethylamine, in an appropriate solvent or solvent mixture, such as toluene, an alcohol, e.g. methanol, an ether, e.g. tetrahydrofuran or 1,4-dioxane, or dichloromethane at temperatures e.g. in the range of from −20° C. to the reflux temperature of the reaction mixture, e.g. from 0 to 30° C.

In a preferred embodiment thereof, the obtained compound is of formula (III-a)*, or a salt thereof

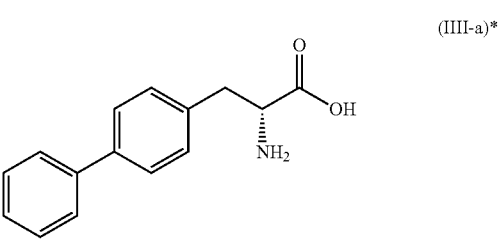 [SMILES: N[C@H](Cc1ccc(-c2ccccc2)cc1)C(=O)O]

(IIII-a)* which is first converted into a compound of formula (III-a)**, or a salt thereof

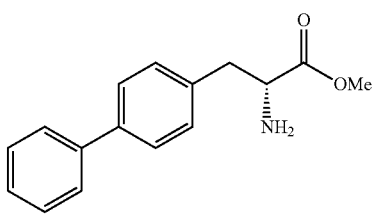
(IIII-a)**

by a process comprising a reaction with methanol,
and then subsequently converted into a compound of formula (II-a)**, or a salt thereof

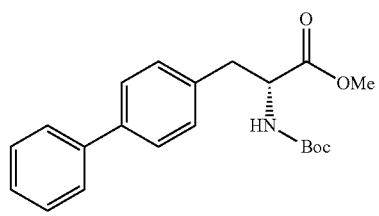
(II-a)* by reaction of the compound of formula (III-a)** with di-tert-butyl dicarbonate.

In a further embodiment thereof, according to SCHEME 2* and SCHEME 2*-a, step e, the now obtained compound of formula (II), or a salt thereof

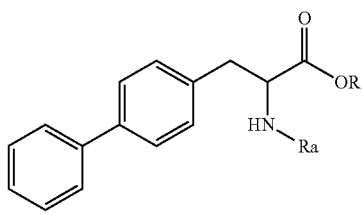
(II)

preferably a compound of formula (II-a), or a salt thereof

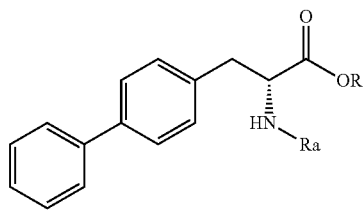
(II-a)

wherein in both formulae R is optionally substituted $C_1$-$C_7$-alkyl, $C_6$-$C_{10}$-aryl or $C_6$-$C_{10}$-aryl-$C_1$-$C_7$-alkyl, preferably unsubstituted $C_6$-$C_{10}$-aryl or $C_6$-$C_{10}$-aryl-$C_1$-$C_7$-alkyl, and Ra is a nitrogen protecting group, is converted into a compound of formula (I), or a salt thereof

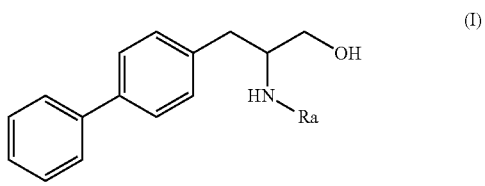
(I)

preferably a compound of formula (I-a), or a salt thereof

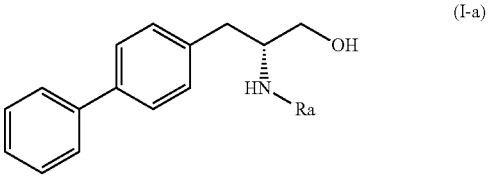
(I-a)

wherein in both formulae Ra is a nitrogen protecting group, by a process comprising reduction of the compound of formula (II) and (II-a), respectively, in the presence of a reducing agent.

In one embodiment thereof, the reduction of the esterified carboxylic group is carried out with the use of complex hydrides, such as an alkali metal borohydride, e.g. sodium borohydride, lithium borohydride, potassium borohydride, or an alkali metal aluminium hydride, such as lithium aluminium hydride, or borane or borane complexes, or alkyl aluminium hydrides, such as DIBAL. The reaction preferably takes place in a customary solvent or solvent mixture, e.g. an ether, such as tetrahydrofuran or methyl-tetrahydrofuran, or a mixture of an ether, such as tetrahydrofuran, and an alcohol, such as ethanol, optionally in the presence of an additive, e.g. an alkali halide, such as lithium chloride, at appropriate temperatures, e.g. in the range from −20 to 40° C., e.g. from 0 to 25° C. Alternatively, reduction can also be achieved by hydrogenation in the presence of appropriate metal catalysts such as Pd/C.

In a preferred embodiment, the compound of formula (II-a)**

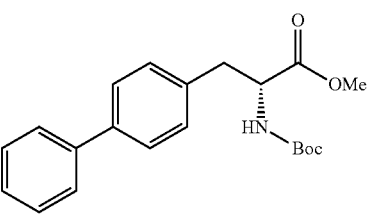
(II-a)**

is reduced by using sodium borohydride to obtain the compound of formula (I-a)*

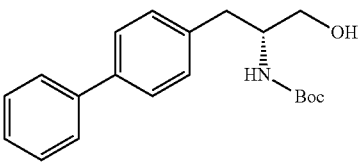
(I-a)*

In a third embodiment thereof, according to SCHEME 2 and SCHEME 2-a, step e*, the obtained compound of formula (III), or a salt thereof

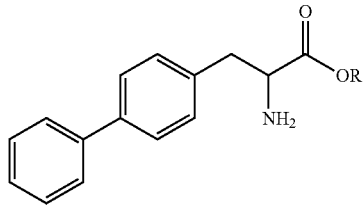
(III)

preferably a compound of formula (III-a), or a salt thereof

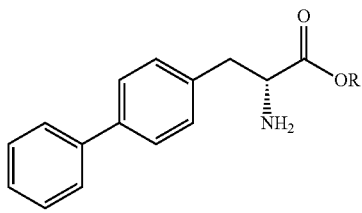
(III-a)

wherein in both formulae R is hydrogen or a carboxyl protecting group,
is converted into a compound of formula (I*), or a salt thereof

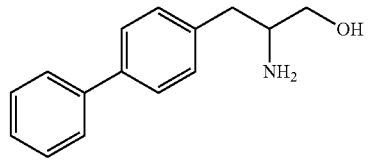
(I*)

preferably a compound of formula (I*-a), or a salt thereof

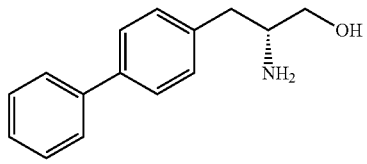
(I*-a)

by a process comprising reduction of the compound of formula (III) in the presence of a reducing agent.

In one embodiment, the reduction is carried out as described above for the reduction reaction according to SCHEME 2 and SCHEME 2-a, step e.

In a preferred embodiment thereof, the compound of formula (III-a)*

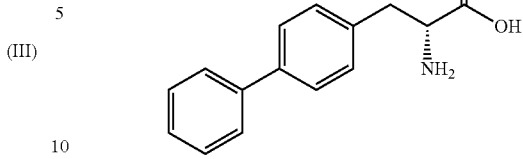
(III-a)* is activated by reaction with isobutyl chloroformate in the presence of N-methylmorpholine, followed by reduction using sodium borohydride to obtain the compound of formula (I*-a)

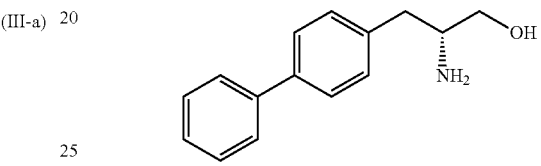
(I*-a)

In a further embodiment thereof, according to SCHEME 2 and SCHEME 2-a, step d*, the now obtained compound of formula (I*), or a salt thereof

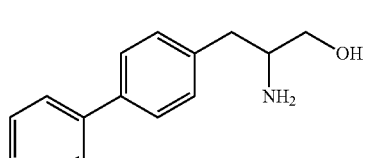
(I*)

preferably the compound of formula (I*-a), or a salt thereof

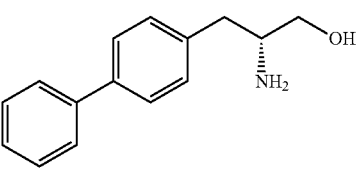
(I*-a)

is converted into a compound of formula (I), or a salt thereof

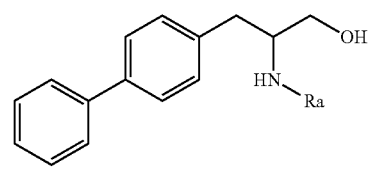
(I)

preferably a compound of formula (I-a), or a salt thereof

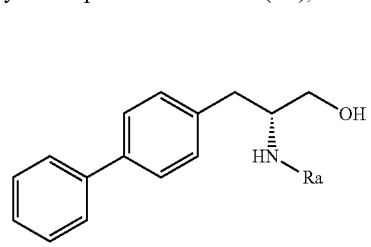
(I-a)

wherein in both formulae Ra is a nitrogen protecting group, by a process comprising introduction of a nitrogen protecting group Ra.

In one embodiment, the compound of formula (I-a) is of formula (I-a)*

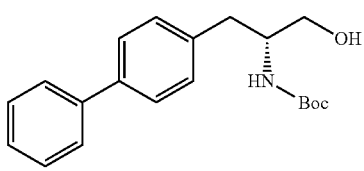
(I-a)* which is obtained by reaction of the compound of formula (I*-a) with di-tert-butyl dicarbonate.

In one embodiment, the introduction of the nitrogen protecting group Ra is carried out as described above for this reaction according to SCHEME 2 and SCHEME 2-a, step d.

Reactions According to SCHEME 3 and SCHEME 3-a:

In the first aspect of the present invention, the compound of formula (I) and (I-a), respectively,

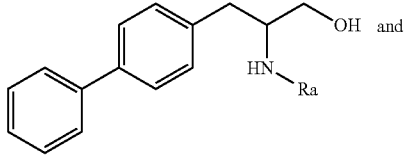
(I) and

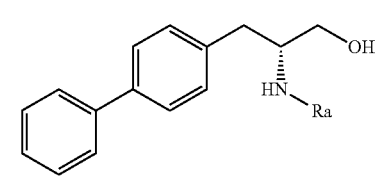
(I-a)

wherein Ra is a nitrogen protecting group, obtained as a result of the transaminase reaction and the reaction steps depicted under SCHEME 2 and SCHEME 2-a, SCHEME 2* and SCHEME 2*-a, and SCHEME 2 and SCHEME 2-a, respectively, can then be converted to a compound of formula (VII) and (VII-a), respectively, or salts thereof, and then further converted into the NEP inhibitor prodrug sacubitril, by a reaction sequence as depicted in SCHEME 3 and SCHEME 3-a, respectively.

Accordingly, in one embodiment thereof, the obtained compound of formula (I), or a salt thereof,

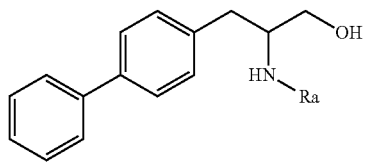
(I)

preferably a compound of formula (I-a), or a salt thereof

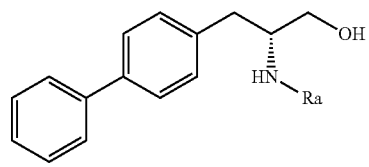
(I-a)

wherein in both formulae Ra is a nitrogen protecting group, is reacted by a process comprising a TEMPO mediated oxidation reaction or an oxidation with Dess-Martin periodinane to obtain a compound of formula (VIII), or a salt thereof,

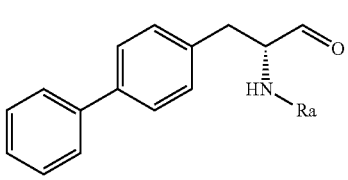
(VIII)

preferably a compound of formula (VIII-a), or a salt thereof

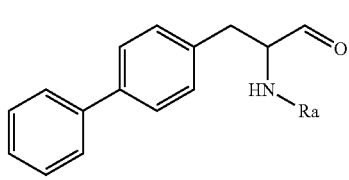
(VIII-a)

wherein in both formulae Ra is hydrogen or a nitrogen protecting group.

Such reaction of the compound of formula (I), or more specifically of formula (I-a) to the corresponding aldehyde is performed by using a TEMPO mediated oxidation (see e.g. WO 2008/031567 or WO 2014/032627, page 24-25) or using alternative reaction conditions, such as oxidation with Dess-Martin periodinane (see e.g. WO 2008/136561).

In a further embodiment thereof, the obtained compound of formula (VIII), or a salt thereof,

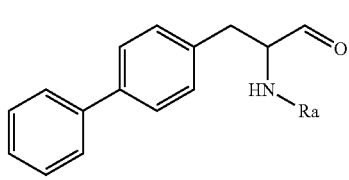
(VIII)

preferably a compound of formula (VIII-a), or a salt thereof
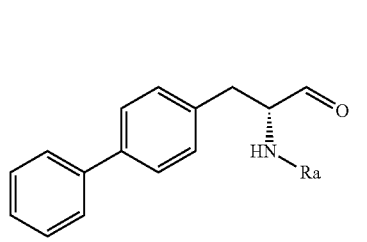
(VIII-a)
is further reacted to prepare N-(3-carboxyl-1-oxopropyl)-(4S)-(p-phenylphenylmethyl)-4-amino-(2R)-methyl butanoic acid ethyl ester, or a salt thereof.
Preferably, said reaction comprises the following steps or steps in analogy thereto (see also WO 2008/031567 or WO 2014/032627, page 24-25):
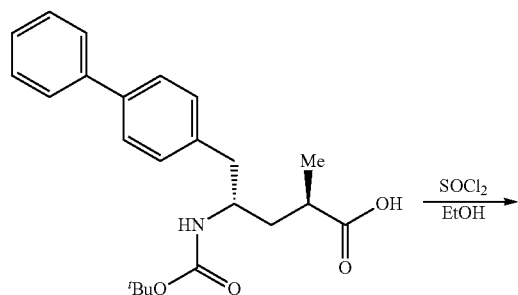
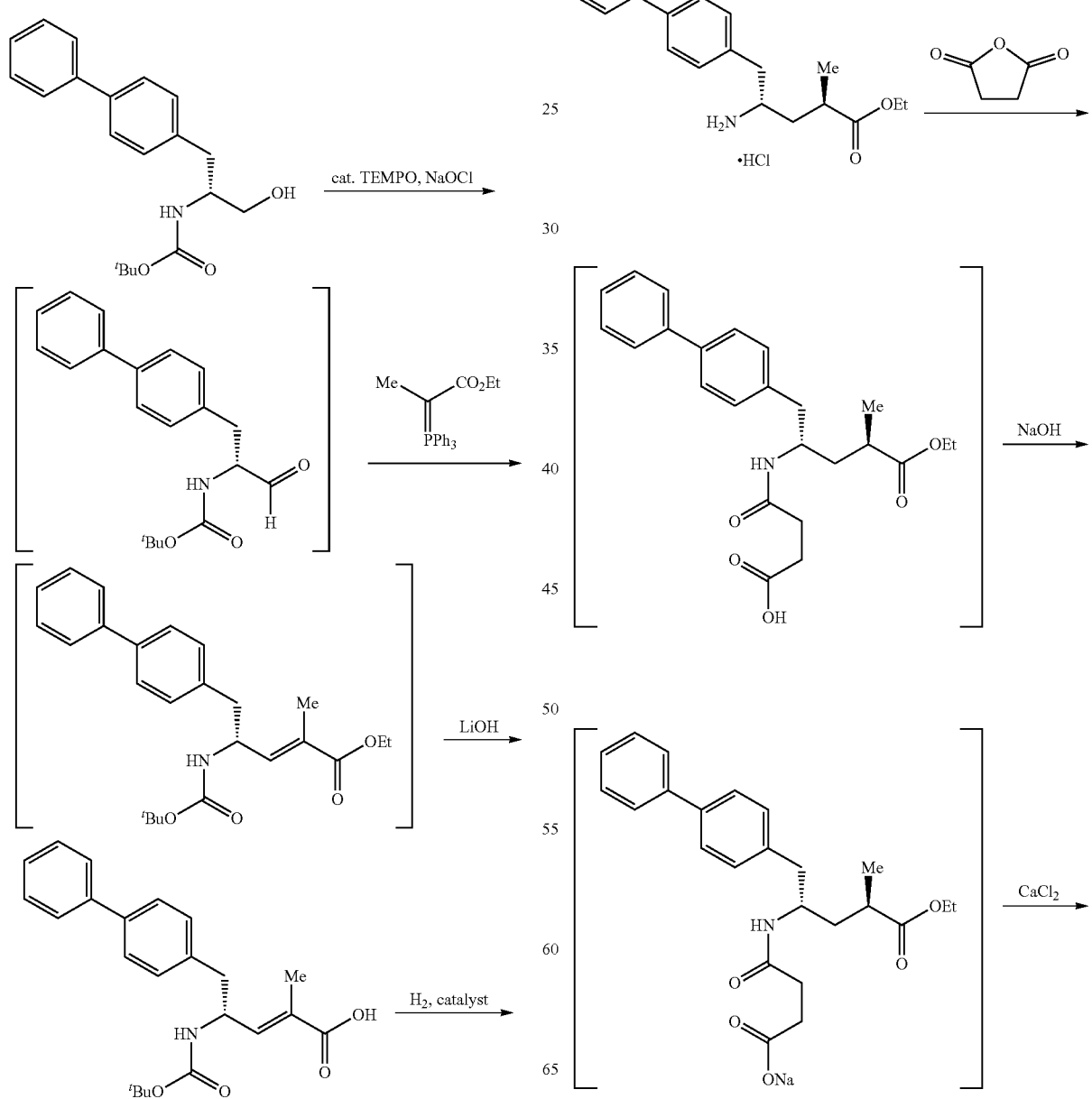

-continued

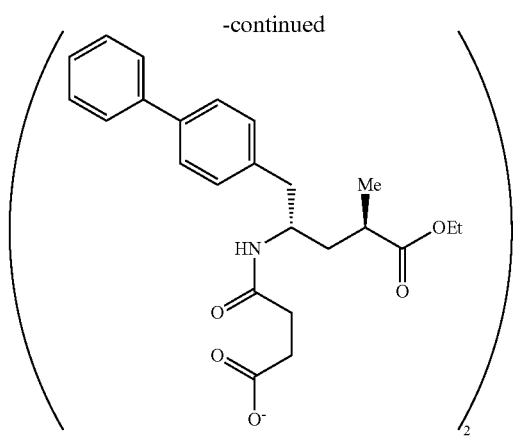

After the aforementioned TEMPO oxidation, the aldehyde of formula (VIII-a) is subjected to a Wittig reaction with carbethoxyethylidene-triphenylphosphorane to deliver (R)-5-biphenyl-4-yl-4-tert-butoxycarbonylamino-2-methyl-pent-2-enoic acid ethyl ester. The ester or—after saponification of the ester—the corresponding free acid (R)-5-biphenyl-4-yl-4-tert-butoxycarbonylamino-2-methylpent-2-enoic acid is then hydrogenated in the presence of a catalyst, whilst preferably producing the preferred diastereoisomer with high selectivity.

Deprotection of the nitrogen functionality, i.e. removal of the Boc group, if necessary re-introduction of the ethyl ester group, and subsequent coupling with succinic anhydride delivers the desired NEP inhibitor prodrug compound or a salt thereof. Optionally, the ester can be saponified to the free acid providing the NEP inhibitor drug compound.

Reactions According to SCHEME 4 and SCHEME 4-a:

in a second aspect, the present invention relates to a process according to SCHEME 4 and SCHEME 4-a:

The reaction step a in both SCHEME 4 and SCHEME 4-a is identical to reaction step a in SCHEME 1 and SCHEME 1-a, respectively, as described above in more detail.

Reaction step b*

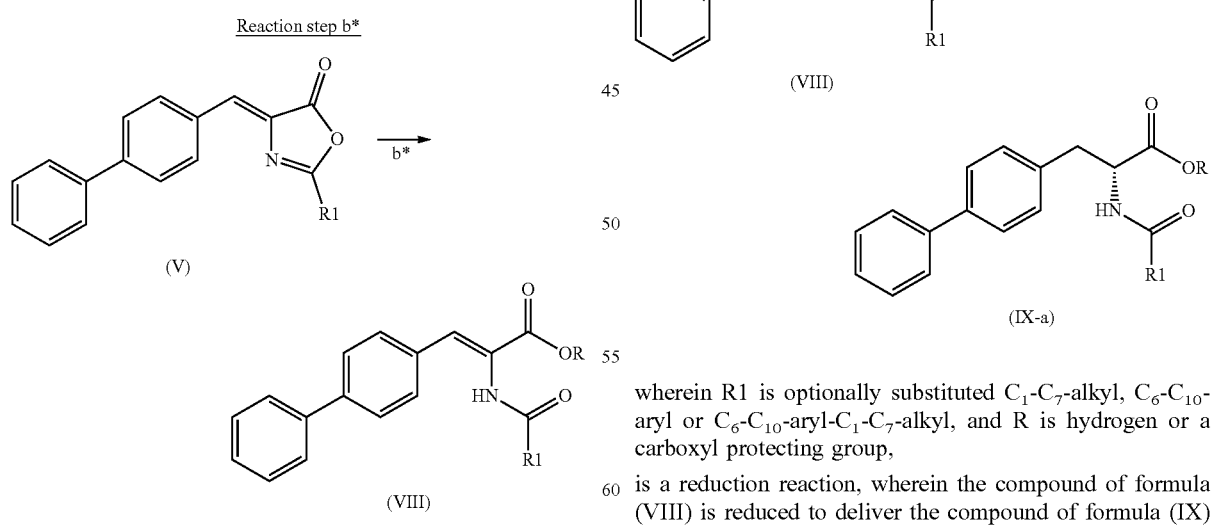

wherein R1 is optionally substituted $C_1$-$C_7$-alkyl, $C_6$-$C_{10}$-aryl or $C_6$-$C_{10}$-aryl-$C_1$-$C_7$-alkyl, and R is hydrogen or a carboxyl protecting group, is a ring opening reaction, wherein the compound of formula (V) is treated with water or an alcohol R—OH to deliver the compound of formula (VIII) according to methods well known in the art and e.g. described generally in WO 2004/002977 (page 17, Scheme 2), in WO 2011/035569 (for the reaction with water, page 4-5), and WO 2013/026773 (Scheme 1, second step), which are incorporated herein by reference.

If R is hydrogen or another substituent is desired, a carboxyl protecting group can be introduced according to the procedures set out herein above.

Reaction step b**

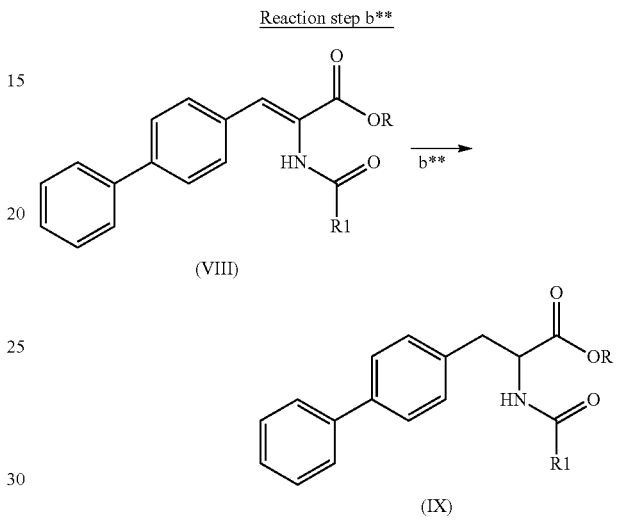

preferably wherein R1 is optionally substituted $C_1$-$C_7$-alkyl, $C_6$-$C_{10}$-aryl or $C_6$-$C_{10}$-aryl-$C_1$-$C_7$-alkyl, and R is hydrogen or a carboxyl protecting group, is a reduction reaction, wherein the compound of formula (VIII) is reduced to deliver the compound of formula (IX) and (IX-a), respectively, according to methods well known in the art and e.g. described in *Adv. Synth. Catal.* 2003, 345, 308-323, WO 02/04466, WO 2009/090251 (Section 6.3.3 or C.2), WO 2011/035569 (step b), and WO 2013/026773 (using asymmetric hydrogenation in the presence of a catalyst), which are incorporated herein by reference.

Reaction step b***

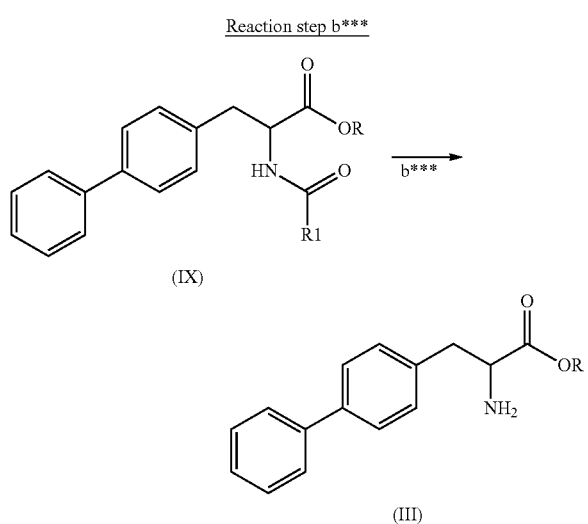

preferably

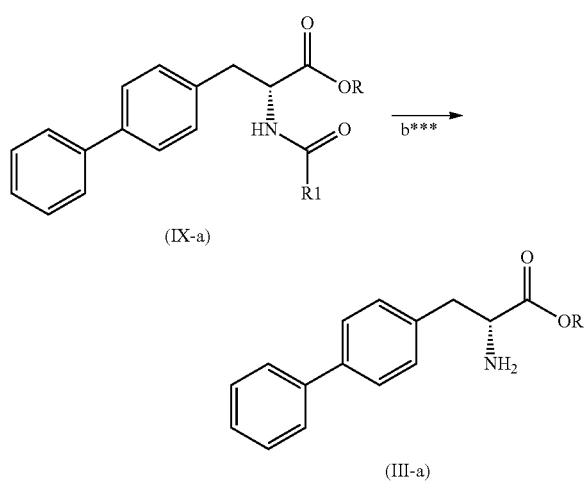

wherein R1 is optionally substituted $C_1$-$C_7$-alkyl, $C_6$-$C_{10}$-aryl or $C_6$-$C_{10}$-aryl-$C_1$-$C_7$-alkyl, and R is hydrogen or a carboxyl protecting group, preferably a $C_1$-$C_7$-alkyl group, comprises then the removal of the acyl group of compound (IX) to deliver the free amino group in compound (III) according to methods well known in the art and e.g. described in Adv. Synth. Catal. 2003, 345, 308-323, and CN101362708A, which are incorporated herein by reference.

The reaction preferably takes place in the presence of an aqueous inorganic acid, e.g. a hydrohalic acid, such as hydrochloric acid, in an appropriate solvent or solvent mixture, e.g. an alcohol, such as methanol, or an ether, such as 1,4-dioxane, or a carboxylic acid, such as acetic acid, and/or water, at preferred temperatures in the range from 0° C. to the reflux temperature of the reaction mixture, e.g. from 20 to 100° C.; or an organic acid, e.g. a sulfonic acid, such as methanesulfonic acid, in an appropriate solvent, e.g. an alcohol, such as methanol, at preferred temperatures in the range from 50° C. to the reflux temperature of the reaction mixture, e.g. from 60 to 70° C.

The reaction step d in both SCHEME 4 and SCHEME 4-a, namely the introduction of the nitrogen protecting group Ra into the compound of formula (III) to deliver the compound of formula (II), is identical to reaction step d in SCHEME 2 and SCHEME 2-a, respectively, as described above in more detail, and anyway well known in the art.

The reaction step e in both SCHEME 4 and SCHEME 4-a, namely the reduction of the carboxylic group in the compound of formula (II) to the protected amino alcohol compound of formula (I), is identical to reaction step e in SCHEME 2 and SCHEME 2-a, respectively, as described above in more detail. A similar reaction is also described within WO 2008/138561 (page 36), which is incorporated herein by reference.

The reaction step f and the subsequent steps in both SCHEME 4 and SCHEME 4-a, namely the oxidation of the protected amino alcohol compound of formula (I) to the corresponding aldehyde of formula (VII) and subsequent transformation to the NEP inhibitor prodrug sacubitril, is identical to the reaction sequence as depicted in SCHEME 3 and SCHEME 3-a, respectively, as described above in more detail and anyway well known in the art.

FURTHER EMBODIMENTS

In any of the aforementioned processes according to SCHEMEs 1 to 4-a, in one embodiment, R1 is a nitrogen protecting group selected from $C_1$-$C_6$-alkyl, which is unsubstituted or mono-, di- or tri-substituted by tri-$C_1$-$C_6$-alkyl-silyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O) or S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$;
$C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl, and silyl,
wherein each silyl group is a SiR11R12R13 group, wherein R11, R12 and R13 are, independently of each other, $C_1$-$C_7$-alkyl, $C_6$-$C_{10}$-aryl or phenyl-$C_1$-$C_4$-alkyl.

In a preferred embodiment thereof, R1 is $C_1$-$C_7$-alkoxycarbonyl, especially tert-butoxycarbonyl (Boc).

In any of the aforementioned reaction schemes, any of the obtained chiral compounds (I), (II), (III), (VII) and (IX) depicted without specific configuration at the carbon atom carrying the amino group can be resolved into the corresponding pure enantiomer of the formula (I-a), (II-a), (III-a), (VII-a) or (IX-a) by using customary methods for the resolution of enantiomers from enantiomer mixtures (such as racemates), e.g. by selective crystallization (e.g. via diastereomeric salts) from solutions or emulsions or chiral chromatography. Such methods are well-known in the art.

EXAMPLES

The following examples illustrate the invention without limiting its scope.
Abbreviations used:
Aq., aq. Aqueous
Ac acetyl
Bu butyl
CDI N,N-carbonyldiimidazole
Et ethyl
h hour(s)
Me methyl min minute(s)
Ph phenyl Overview I

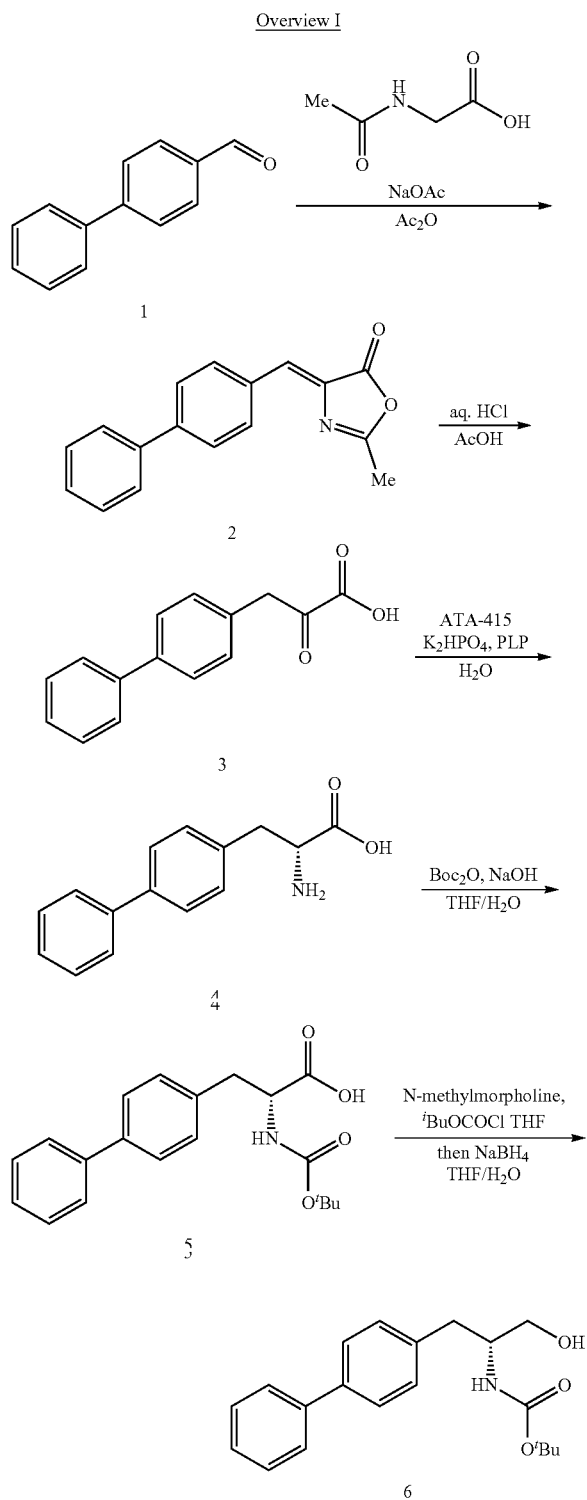

Example 1: Manufacture of (Z)-4-([1,1'-biphenyl]-4-ylmethylene)-2-methyloxazol-5(4H)-one 2

A suspension of biphenyl-4-carboxaldehyde 1 (e.g. Sigma-Aldrich, catalogue no. 834680, CAS no. 3218-36-8) (25.1 g, 135.0 mmol), N-acetylglycine (16.2 g, 138.3 mmol) and anhydrous sodium acetate (11.1 g, 135.3 mmol) in acetic anhydride (250 mL) was heated to 110-120° C. and stirred at this temperature for 10 h. The reaction mixture was cooled to 5° C., and the precipitated solids were filtered off, washed with cold diisopropyl ether and dried at 50° C. under vacuum to give the product 2 as a yellow-orange solid (36.5 g, quantitative). The crude product obtained was taken for the next step without further purification.

$^1$H-NMR (400 MHz, DMSO-d6): δ ppm 2.42 (s, 3H), 7.28 (s, 1H), 7.37-7.45 (m, 2H), 7.47-7.54 (m, 2H), 7.73-7.79 (m, 2H), 7.83 (m, 2H), 8.28 (m, 2H) ppm.

Example 2: Manufacture of 3-([1,1'-biphenyl]-4-yl)-2-oxopropanoic acid 3

A suspension of (Z)-4-([1,1'-biphenyl]-4-ylmethylene)-2-methyloxazol-5(4H)-one 2 (20.0 g, 75.96 mmol) in acetic acid (60 mL) and 37% aqueous HCl (140 mL) was heated to 80-100° C. and stirred at this temperature for 10 h. The reaction mixture was cooled to room temperature, then water (200 mL) was added. The precipitated solids were filtered off, washed with cold water and dried at 50° C. under vacuum to give the product 3 as an orange solid (9.83 g, 53.9% yield).

$^1$H-NMR (400 MHz, DMSO-d6): δ 6.45 (s, 1H), 7.33-7.40 (m, 1H), 7.46 (m, 2H), 7.64-7.73 (m, 4H), 7.85 (m, 2H), 9.34 (s, 1H), 13.23 (br. s, 1H) ppm; MS (ES-API): positive mode 258.1 [M+NH$_4$]$^+$; MS (ES-API): negative mode 239.2 [M−H]$^-$.

Example 3: (R)-3-([1,1'-Biphenyl]-4-yl)-2-aminopropanoic acid 4

Variant a)

Isopropylamine hydrochloride (19.95 g, 208.8 mmol) were dissolved in aqueous 67 mM K$_2$HPO$_4$ solution (210 mL; pH 9.39), then pyridoxal 5'-phosphate (PLP) (54 mg) was added. The pH value was adjusted to pH 9 by addition of isopropylamine. 3-([1,1'-Biphenyl]-4-yl)-2-oxopropanoic acid 3 (1.00 g, 4.167 mmol) was suspended in 200 mL of this buffer solution and shaken for 5 min at 40° C. and 180 rpm. The transaminase ATA-415 (34 mg; commercially available from Codexis, Inc., Redwood City, Calif., USA) was added, and the reaction mixture was shaken at room temperature for 18 h. The mixture was centrifuged, the solid was resuspended in water (5 mL) and filtered. The resulting white solid was dried under vacuum to give the product 4 (1.13 g, 90% yield) as the corresponding isopropylammonium chloride salt.

$^1$H-NMR (400 MHz, DMSO-d6): δ 3.18 (d, 2H), 4.21 (br. t, 1H), 7.34-7.41 (m, 3H), 7.44-7.51 (m, 2H), 7.61-7.70 (m, 4H), 8.46 (br. s, 3H), 13.41-14.37 (m, 1H) ppm (determined as hydrochloride); enantiomeric purity (HPLC): >99%.

Variant b)

Isopropylamine hydrochloride (19.95 g, 208.8 mmol) was dissolved in aqueous 67 mM K$_2$HPO$_4$ solution (105 mL; pH 9.39), then pyridoxal 5'-phosphate (PLP) (27 mg) was added. The pH value was adjusted to pH 9 by addition of isopropylamine, giving buffer solution A. 3-([1,1'-Biphenyl]-4-yl)-2-oxopropanoic acid 3 (80 mg, 0.333 mmol) was suspended in 2 mL of buffer solution A and shaken for 10 min at 40° C. The pH value was adjusted to pH 8.15 by addition of isopropylamine. Isopropylamine hydrochloride (4.75 g, 49.70 mmol) and pyridoxal 5'-phosphate (PLP) (6.25 mg) were dissolved in 0.1 M triethylamine buffer (25 mL; pH 7.0), giving buffer solution B. Transaminase ATA- 032 (6.4 mg; commercially available from Codexis) was dissolved in buffer solution B (640 µL), shaken at 30° C. for 5 min and centrifuged. The solution of transaminase ATA-032 (100 µL) was added, and the reaction mixture was shaken at 40° C. and 180 rpm for 17 h. Analysis of the reaction mixture by HPLC indicated 100% conversion and >99% ee.

Physical Data See Variant a)

Variant c)

98% Sulfuric acid (45.0 g, 450 mmol, 0.54 equiv.) is slowly added to water (300 g), followed by $K_2HPO_4 \cdot 3H_2O$ (47.5 g, 208 mmol, 0.25 equiv.) and compound 3 (200 g, 832 mmol, 1.00 equiv.). To the resulting suspension is added 70% aqueous isopropylamine solution (147.6 g, 1748 mmol, 2.10 equiv.). After heating to 45° C., the pH is adjusted to pH 8.8-8.9, then Tween 20 (30.0 g) in water (70.0 g) is added. PLP monohydrate (1.68 g, 6.80 mmol, 0.008 equiv.) is charged, followed by adjustment to pH 8.5-8.6. A suspension of ATA-032 (2.00 g) in pH 8 buffer solution (40 mL, prepared from $K_2HPO_4 \cdot 3H_2O$ and water) is added, and the reaction mixture is stirred at 41° C. for 18 h. An aqueous 1 M sulfuric acid solution (1270 g) is charged, and the reaction mixture is subsequently heated to 95° C. and kept at this temperature for 10 h. After cooling to 25° C., the solids are filtered off, and the cake is washed with water (1400 mL), a mixture of 1% aqueous $K_2HPO_4$ $3H_2O$ solution (1400 mL) and 2-butanone (320 g) and 2-butanone (640 g), then dried to give compound 4.

Physical Data See Variant a)

Example 4: Manufacture of (R)-3-([1,1'-biphenyl]-4-yl)-2-((tert-butoxycarbonyl)amino)-propanoic acid 5

To a suspension of (R)-3-([1,1'-biphenyl]-4-yl)-2-aminopropanoic acid 4 (0.9 g, 2.996 mmol; as the corresponding isopropylammonium chloride salt) in tetrahydrofuran (9 mL) and water (9 mL) at room temperature was added a solution of Boc anhydride (0.91 g, 4.103 mmol) in tetrahydrofuran (2 mL), followed by a solution of sodium hydroxide (335 mg, 8.206 mmol) in water (2 mL). The resulting clear solution was stirred at room temperature for 18 h, then 10% aqueous HCl was added to adjust the pH value to pH 4. The organic solvents were removed under vacuum, and the aqueous residue was extracted with ethyl acetate. The combined organic layers were dried over $MgSO_4$, filtered and concentrated under vacuum to give product 5 (1.28 g, quantitative) as a beige solid.

$^1$H-NMR (400 MHz, DMSO-d6): δ 1.32 (s, 9H), 2.87 (dd, 1H), 3.06 (dd, 1H), 4.13 (ddd, 1H), 7.15 (d, 1H), 7.31-7.39 (m, 3H), 7.45 (m, 2H), 7.58 (m, 2H), 7.64 (m, 2H), 12.63 (br. s, 1H).

Example 5: Manufacture of (R)-tert-butyl (1-([1,1'-biphenyl]-4-yl)-3-hydroxypropan-2-yl)carbamate 6

To a solution of (R)-3-([1,1'-biphenyl]-4-yl)-2-((tert-butoxycarbonyl)amino)-propanoic acid 5 (1.28 g, corresponding to 2.996 mmol) in tetrahydrofuran (8 mL) at −15° C. was added isobutyl chloroformate (539 mg, 3.749 mmol), followed by N-methylmorpholine (402 mg, 3.937 mmol). A precipitate formed, and after stirring at −15° C. for 30 min, the precipitate was filtered off, followed by washing of the cake with THF. The filtrate was added over 1 h to a solution of sodium borohydride (296 mg, 7.499 mmol) in water (4 mL) at 0° C. The reaction mixture was stirred at 0° C. for 1 h, then water (15 mL) was added, and the reaction mixture was extracted with ethyl acetate. The combined organic layers were dried over $MgSO_4$, filtered and concentrated under vacuum to provide the crude product. Purification by chromatography (silica gel, heptanes/ethyl acetate) gave product 6 (0.74 g, 75% yield over two steps) as a white solid.

$^1$H-NMR (400 MHz, DMSO-d6): δ 1.32 (s, 9H), 2.60 (dd, 1H), 2.86 (dd, 1H), 3.24-3.31 (m, 1H), 3.33-3.42 (m, 1H), 3.52-3.70 (m, 1H), 4.72 (t, 1H), 6.56-6.71 (m, 1H), 7.28 (m, 2H), 7.30-7.38 (m, 1H), 7.44 (m, 2H), 7.56 (m, 2H), 7.60-7.66 (m, 2H); MS (ES-API): positive mode 350.3 [M+Na]$^+$.

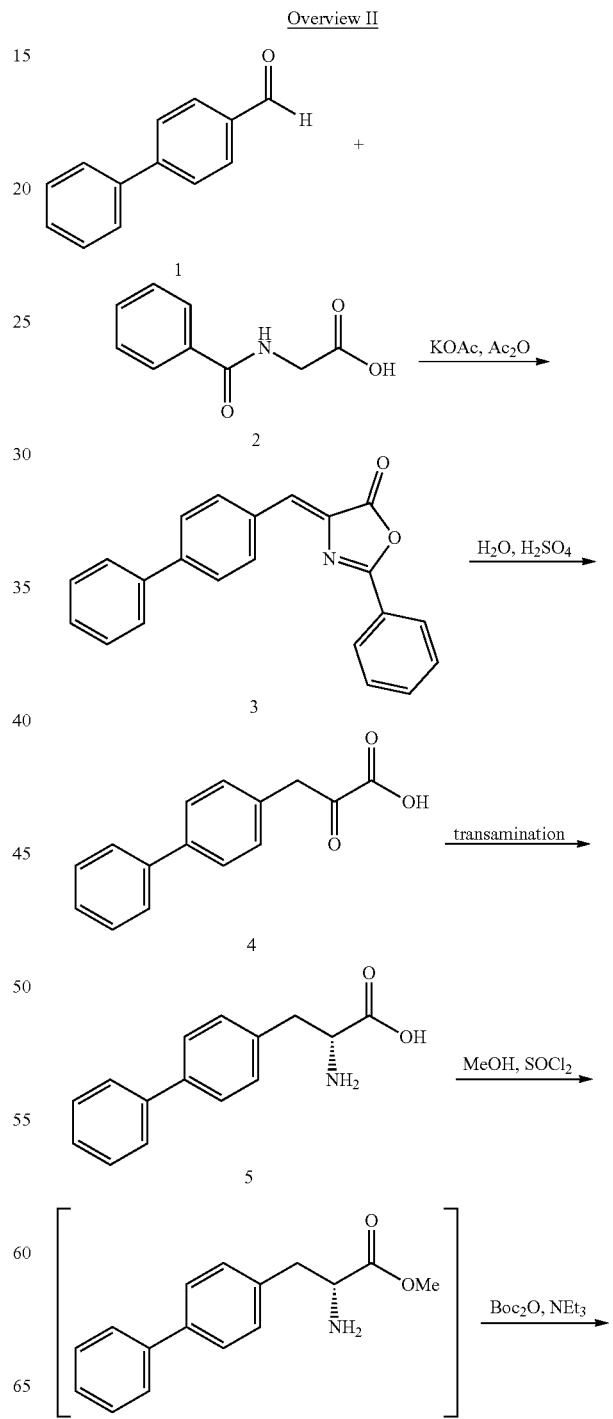

Overview II

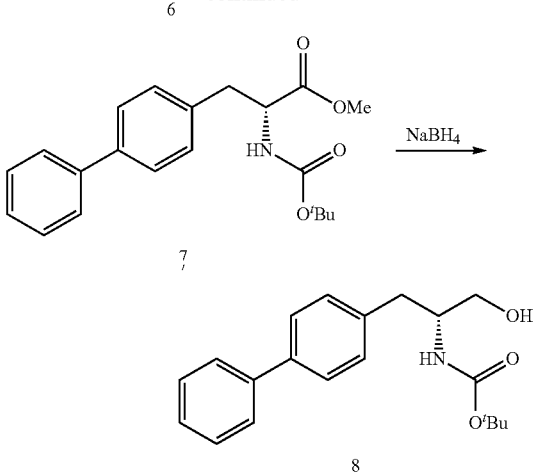

Example 6: Synthesis of (Z)-4-([1,1'-biphenyl]-4-ylmethylene)-2-benzyloxazol-5(4H)-one 3

[1,1'-Biphenyl]-4-carbaldehyde 1 (90.0 g, 493.9 mmol, 1.0 equiv.), 2-benzamidoacetic acid 2 (106.2 g, 592.7 mmol, 1.2 equiv.), potassium acetate (19.4 g, 197.7 mmol, 0.4 equiv.) and toluene (720 mL) are charged into the reactor. The reaction mixture is heated to 55-65° C., then acetic anhydride (32.6 mL, 345.8 mmol, 0.6 equiv.) is added over 1 h, leading to formation of a white suspension. After stirring for 2 h, the reaction mixture is cooled to 45-55° C. over 1 h. Seed crystals are added, and the reaction mixture is stirred for another 1 h. More acetic anhydride (107.2 mL, 113.6 mmol, 2.4 equiv.) is added over 2 h, followed by stirring for another 6 h. The reaction mixture is subsequently cooled to 15-25° C. over 2.5 h, and the solids are filtered off. The cake is washed with toluene (90 mL, twice), then dried to give compound 3.

Example 7: Synthesis of 3-([1,1'-biphenyl]-4-yl)-2-oxopropanoic acid 4

Compound 3, 68% aqueous sulfuric acid (803 mL, 8.85 mol, 18.0 equiv. based on compound 1) and acetic acid (576 mL) are charged into the reactor. The reaction mixture is heated to 95-105° C. and stirred for another 10 h. The reaction mixture is subsequently cooled to ca. 25° C. over 5 h. Methyl tert-butyl ether (778 mL) is added over 2 h, and the reaction mixture is further stirred for 3 h. The solids are filtered off, and the cake is washed with water (500 mL), 0.2% aqueous dipotassium hydrogenphosphate solution (300 mL) and water (300 mL), then dried to give compound 4.

Example 8: Synthesis of (R)-3-([1,1'-Biphenyl]-4-yl)-2-aminopropanoic acid 5

98% Sulfuric acid (45.0 g, 450 mmol, 0.54 equiv.) is slowly added to water (300 g), followed by $K_2HPO_4 \cdot 3H_2O$ (47.5 g, 208 mmol, 0.25 equiv.) and compound 4 (200 g, 832 mmol, 1.00 equiv.). To the resulting suspension is added 70% aqueous isopropylamine solution (147.6 g, 1748 mmol, 2.10 equiv.). After heating to 45° C., the pH is adjusted to pH 8.8-8.9, then Tween 20 (30.0 g) in water (70.0 g) is added. PLP monohydrate (1.68 g, 6.80 mmol, 0.008 equiv.) is charged, followed by adjustment to pH 8.5-8.6. A suspension of ATA-032 (2.00 g) in pH 8 buffer solution (40 mL, prepared from $K_2HPO_4 \cdot 3H_2O$ and water) is added, and the reaction mixture is stirred at 41° C. for 18 h. An aqueous 1 M sulfuric acid solution (1270 g) is charged, and the reaction mixture is subsequently heated to 95° C. and kept at this temperature for 10 h. After cooling to 25° C., the solids are filtered off, and the cake is washed with water (1400 mL), a mixture of 1% aqueous $K_2HPO_4 \cdot 3H_2O$ solution (1400 mL) and 2-butanone (320 g) and 2-butanone (640 g), then dried to give compound 5.

Example 9: Synthesis of (R)-3-([1,1'-biphenyl]-4-yl)-2-((tert-butoxycarbonyl)amino)propanoic acid methyl ester 7

Compound 5 (20.00 g, 82.9 mmol, 1.0 equiv.) and methanol (160 mL) are charged into a reactor. The resulting suspension, is heated to 50° C., then thionyl chloride (12.82 g, 107.7 mmol, 1.3 equiv.) is added dropwise during 30 min. Stirring is continued for 10 h at 50-55° C., then triethylamine (29.36 g, 290.1 mmol, 3.5 equiv.) is added at 50° C., followed by toluene (100 mL). Methanol is removed under vacuum by distillation at 50° C. The reaction mixture is cooled to 20° C., then Boc anhydride (19.9 g, 91.2 mmol, 1.1 equiv.) is added, and the reaction is further stirred at 20° C. for 2 h. The reaction is quenched by addition of 10% aqueous NaCl solution (100 mL), and the phases are separated. The organic layer is washed with 10% aqueous NaCl solution (50 mL), then partially concentrated and diluted with heptane fraction (120 mL) at 50° C. The reaction mixture is cooled to 10° C. over 5 h, and the formed solids are filtered off, washed with heptane fraction (20 mL) and dried to give compound 7.

$^1$H-NMR (400 MHz, DMSO-d6): δ 1.32 (s, 9H), 2.89 (dd, 1H), 3.04 (dd, 1H), 3.63 (s, 3H), 4.21 (ddd, 1H), 7.29-7.38 (m, 4H), 7.41-7.47 (m, 2H), 7.55-7.61 (m, 2H), 7.61-7.67 (m, 2H); MS (ES-API): positive mode 356.4 [M+H]$^+$.

Example 10: Synthesis of (R)-tert-butyl (1-([1,1'-biphenyl]-4-yl)-3-hydroxypropan-2-yl)-carbamate 8

To a solution of compound 7 (1.00 g, 2.81 mmol, 1.00 equiv.) in methyl-THF (5.0 mL) at 0° C. is added sodium borohydride (319 mg, 8.43 mmol, 3.00 equiv.) at 0-5° C. to provide a white suspension. Methanol (0.7 mL, 17.3 mmol, 6.15 equiv.) is added slowly, leading to gas evolution. The reaction mixture is slowly warmed to 20-25° C., then stirred at this temperature until complete conversion. The reaction mixture is cooled to 0° C., then aqueous 40% citric acid (6.0 mL) is added slowly, leading to vigorous gas evolution. The phases are separated, and the organic phase is washed with water (3.0 mL). The solvent is changed to toluene (5.0 mL), then heptane fraction (5.0 mL) is added to precipitate compound 8. The product is filtered off, washed with heptane fraction and dried to give compound 8.

Overview III

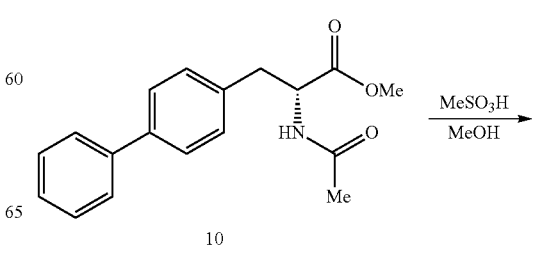

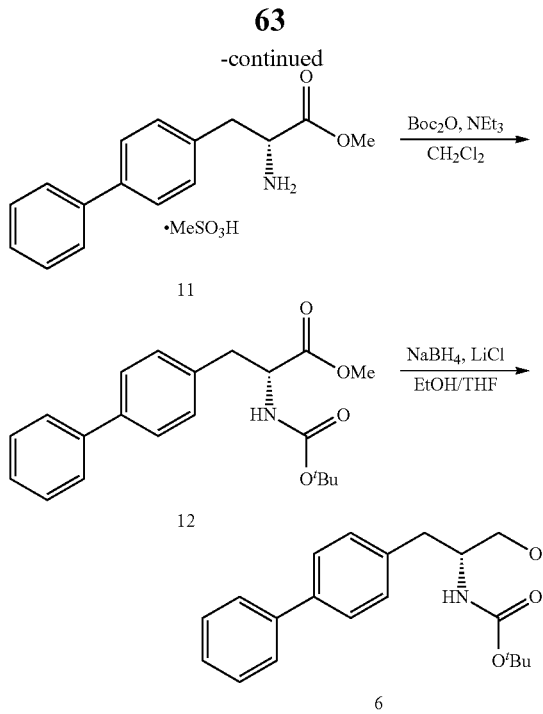

Example 11: Manufacture of (R)-methyl 3-([1,1'-biphenyl]-4-yl)-2-aminopropanoate methanesulfonate 11

A suspension of (R)-methyl 3-([1,1'-biphenyl]-4-yl)-2-acetamidopropanoate 10 (0.190 g, 0.639 mmol) in methanol (1.2 mL) at 40° C. was treated with methanesulfonic acid (0.070 g, 1.078 mmol). The reaction mixture was heated to reflux and kept at this temperature for 21 h. After cooling to 50° C., a mixture of isopropanol and heptanes 1:1 (10 mL) was added, leading to formation of a white precipitate. The reaction mixture was further cooled to 0° C., the solids were filtered off and washed with a cold mixture of isopropanol and heptanes 1:1. Drying at 50° C. under vacuum provided product 11 (0.150 g, 67% yield) as a grey solid.

$^1$H-NMR (400 MHz, DMSO-d6): δ 2.30 (d, 4H), 3.14 (m, 2H), 3.73 (s, 3H), 4.39 (t, 1H), 7.32 (m, 2H), 7.38 (m, 1H), 7.44-7.52 (m, 2H), 7.63-7.71 (m, 4H), 8.41 (br. s, 3H); MS (ES-API): positive mode 256.2 [M+H]$^+$.

Example 12: Manufacture of (R)-methyl 3-([1,1'-biphenyl]-4-yl)-2-((tert-butoxycarbonyl)amino)propanoate 12

To a suspension of (R)-methyl 3-([1,1'-biphenyl]-4-yl)-2-aminopropanoate methanesulfonate 11 (0.136 g, 0.378 mmol) in dichloromethane (2 mL) at room temperature was added triethylamine (0.054 mL, 0.395 mmol), followed by Boc anhydride (0.093 mL, 0.401 mmol). The reaction mixture was stirred at 30° C. for 4.5 h. Following addition of saturated aqueous ammonium chloride solution (5 mL) and ethyl acetate (5 mL), the phases were separated. The aqueous phase was extracted with ethyl acetate, and the combined organic layers were dried over Na$_2$SO$_4$, filtered and concentrated under vacuum to give product 12 (0.148 g, quantitative) as a beige solid.

$^1$H-NMR (400 MHz, DMSO-d6): δ, 1.32 (s, 9H), 2.85-2.93 (m, 1H), 3.00-3.08 (m, 1H), 3.63 (s, 3H), 4.16-4.25 (m, 1H), 7.27-7.38 (m, 4H), 7.40-7.49 (m, 2H), 7.58 (m, 2H), 7.62-7.68 (m, 2H); MS (ES-API): positive mode 356.3 [M+H]$^+$.

Example 8: Manufacture of (R)-tert-butyl (1-([1,1'-biphenyl]-4-yl)-3-hydroxypropan-2-yl)carbamate 6

To a solution of (R)-methyl 3-([1,1'-biphenyl]-4-yl)-2-((tert-butoxycarbonyl)-amino)propanoate 12 (0.140 g, mmol) in a mixture of ethanol and tetrahydrofuran 1:1 (2 mL) at room temperature was added lithium chloride hydrate (0.183 g, mmol), followed by sodium borohydride (0.109 g, mmol). The reaction mixture was stirred at 25° C. for 27 h. The reaction mixture was diluted with a mixture of ethanol and tetrahydrofuran 1:1, the solids were filtered off and washed with a mixture of ethanol and tetrahydrofuran 1:1. The clear filtrate was concentrated under vacuum to give product 6 (0.080 g, 67% yield over two steps).

For analytical data, see preparation of compound 6 from compound 5 above.

The invention claimed is:

1. A process for preparing a compound of formula (III), or a salt thereof,

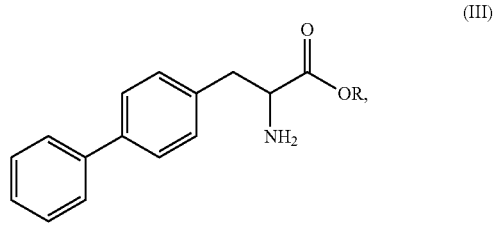

wherein R is hydrogen or a carboxyl protecting group, comprising, converting a compound of formula (IV), or a salt thereof,

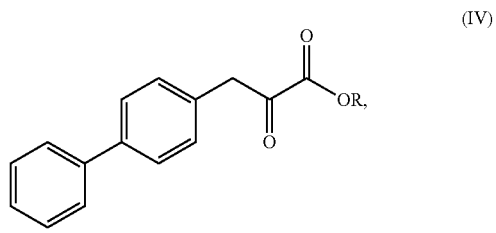

wherein R is hydrogen or a carboxyl protecting group, into the compound of formula (III) by bringing it in contact with an (R)-selective ω-transaminase in the presence of an amine donor, wherein the conversion rate from the compound of formula (IV) to the compound of formula (III) is more than 50%.

2. The process according to claim 1, wherein the amine donor is an achiral amine donor selected from the group consisting of achiral $C_1$-$C_7$-alkylamine, achiral $C_3$-$C_8$-cycloalkylamine, achiral $C_6$-$C_{10}$-aryl-$C_1$-$C_7$-alkylamine, achiral $C_1$-$C_7$-alkyldiamine, achiral amino-$C_1$-$C_7$-alkanoic acid, and achiral $C_6$-$C_{10}$-aryl-di($C_1$-$C_7$-alkylamine).

3. The process according to claim 1, wherein the compound of formula (IV), or a salt thereof,

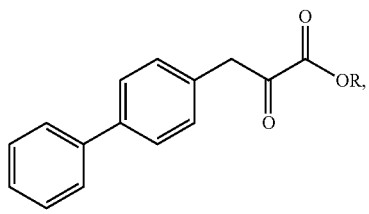

(IV)

wherein R is hydrogen or a carboxyl protecting group,
is obtained by a process comprising hydrolysis of a compound of formula (V),

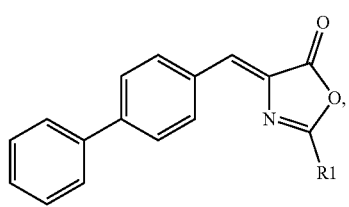

(V)

wherein R1 is $C_1$-$C_7$-alkyl, $C_6$-$C_{10}$-aryl, or $C_6$-$C_{10}$-aryl-$C_1$-$C_7$-alkyl,
under acidic or basic conditions to obtain a compound of formula (IV).

4. The process according to claim 1, wherein the obtained compound of formula (III), or a salt thereof,

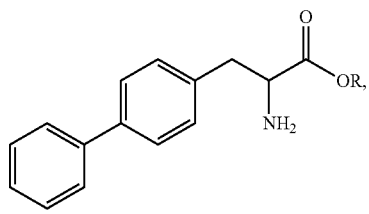

(III)

wherein R is hydrogen or a carboxyl protecting group,
is converted into a compound of formula (II), or a salt thereof,

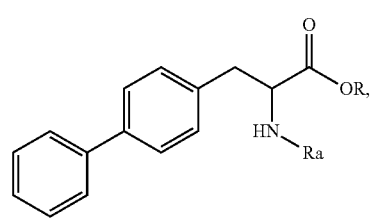

(II)

wherein R is hydrogen or a carboxyl protecting group, and Ra is a nitrogen protecting group,
by a process comprising introduction of a nitrogen protecting group Ra.

5. The process according to claim 1, wherein the obtained compound of formula (III), or a salt thereof,

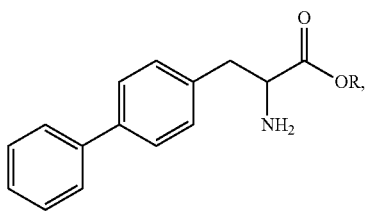

(III)

wherein R is hydrogen,
is first converted into a compound of formula (III), or a salt thereof,

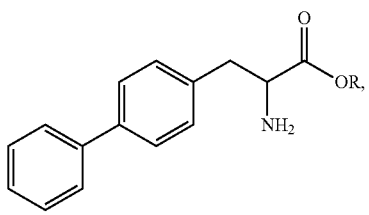

(III)

wherein R is $C_1$-$C_7$-alkyl, $C_6$-$C_{10}$-aryl, or $C_6$-$C_{10}$-aryl-$C_1$-$C_7$-alkyl,
by a process comprising reaction with an alcohol having a formula R—OH, wherein R is $C_1$-$C_7$-alkyl, $C_6$-$C_{10}$-aryl, or $C_6$-$C_{10}$-aryl-$C_1$-$C_7$-alkyl,
which is then subsequently converted into a compound of formula (II), or a salt thereof,

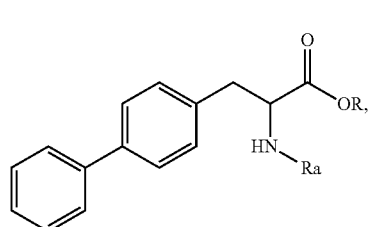

(II)

wherein R is $C_1$-$C_7$-alkyl, $C_6$-$C_{10}$-aryl, or $C_6$-$C_{10}$-aryl-$C_1$-$C_7$-alkyl, and Ra is a nitrogen protecting group,
by a process comprising introduction of a nitrogen protecting group Ra.

6. The process according to claim 1, wherein the obtained compound of formula (III), or a salt thereof,

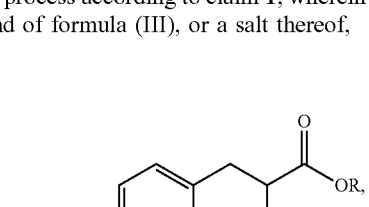

(III)

wherein R is hydrogen or a carboxyl protecting group,
is converted into a compound of formula (I*), or a salt thereof,

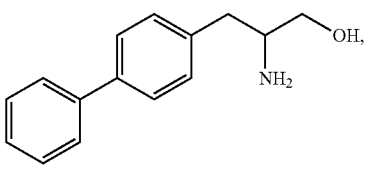
(I*)

by a process comprising reduction of the compound of formula (III) in the presence of a reducing agent.

7. The process according to claim 1, wherein the compound of formula (III) has a formula (IIIa), or a salt thereof:

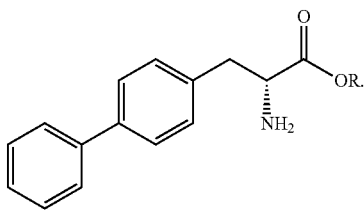
(III-a)

8. The process according to claim 2, wherein the achiral amine donor is isopropylamine (2-aminopropane).

9. The process according to claim 3, wherein the compound of formula (V)

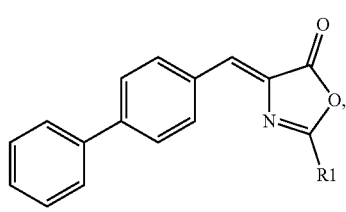
(V)

wherein R1 is $C_1$-$C_7$-alkyl, $C_6$-$C_{10}$-aryl, or $C_6$-$C_{10}$-aryl-$C_1$-$C_7$-alkyl, is obtained by a process comprising reaction of a compound of formula (VI)

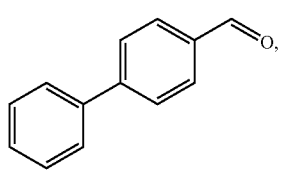
(VI)

with a compound of formula (VII), or a salt thereof,

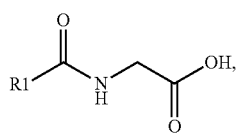
(VII)

wherein R1 is $C_1$-$C_7$-alkyl, $C_6$-$C_{10}$-aryl, or $C_6$-$C_{10}$-aryl-$C_1$-$C_7$-alkyl.

10. The process according to claim 4, wherein the obtained compound of formula (II), or a salt thereof,

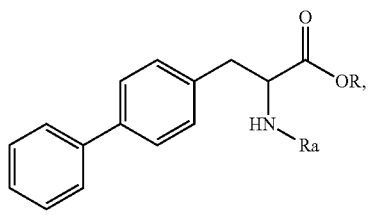
(II)

wherein R is hydrogen or a carboxyl protecting group, and Ra is a nitrogen protecting group, is converted into a compound of formula (I), or a salt thereof,

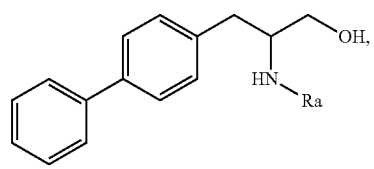
(I)

wherein Ra is a nitrogen protecting group,
by a process comprising reduction of the compound of formula (II) in the presence of a reducing agent.

11. The process according to claim 4, wherein Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

12. The process according to claim 10, wherein the obtained compound of formula (I), or a salt thereof,

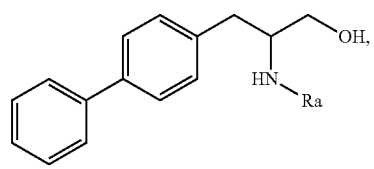
(I)

wherein Ra is a nitrogen protecting group,
is reacted by a process comprising a TEMPO mediated oxidation reaction or an oxidation with Dess-Martin periodinane to obtain a compound of formula (VIII), or a salt thereof,

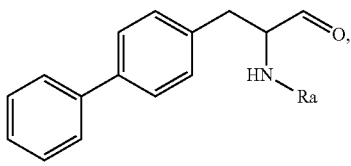

wherein Ra a nitrogen protecting group.

13. The process according to claim 10, wherein Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

14. The process according to claim 5, wherein the obtained compound of formula (II), or a salt thereof,

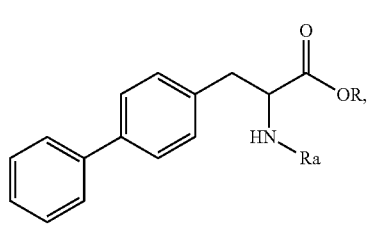

wherein R is $C_1$-$C_7$-alkyl, $C_6$-$C_{10}$-aryl, or $C_6$-$C_{10}$-aryl-$C_1$-$C_7$-alkyl, and Ra is a nitrogen protecting group,
is converted into a compound of formula (I), or a salt thereof,

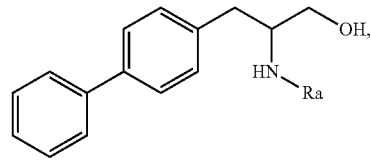

wherein Ra is a nitrogen protecting group,
by a process comprising reduction of the compound of formula (II) in the presence of a reducing agent.

15. The process according to claim 5, wherein Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from the group consisting of N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

16. The process according to claim 14, wherein Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

17. The process according to claim 6, wherein the obtained compound of formula (I*), or a salt thereof,

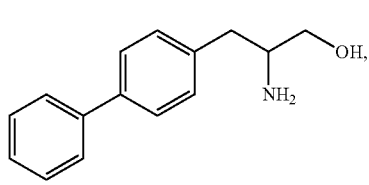

is converted into a compound of formula (I), or a salt thereof

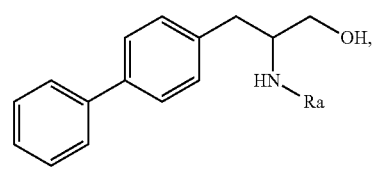

wherein Ra is a nitrogen protecting group,
by a process comprising introduction of a nitrogen protecting group Ra.

18. The process according to claim 17, Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$- alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

19. The process according to claim 12, wherein Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from the group consisting of N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

20. The process according to claim 12, wherein the obtained compound of formula (VIII), or a salt thereof:

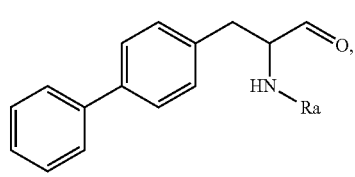

(VIII)

wherein Ra is a nitrogen protecting group, is further reacted to prepare N-(3-carboxyl-1-oxopropyl)-(4S)-(p-phenylphenylmethyl)-4-amino-(2R)-methyl butanoic acid ethyl ester, or a salt thereof.

21. The process according to claim 20, wherein Ra is a nitrogen protecting group selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O), and S(O)$_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$; $C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl; and silyl, wherein each silyl group is a SiR11R12R13 group, wherein R11, R12 and R13 are, independently of each other, $C_1$-$C_7$-alkyl, $C_6$-$C_{10}$-aryl, or phenyl-$C_1$-$C_4$-alkyl.

* * * * *